(12) United States Patent
Holmén

(10) Patent No.: US 6,986,763 B2
(45) Date of Patent: *Jan. 17, 2006

(54) METHODS AND COMPOSITIONS USABLE IN CATARACT SURGERY

(75) Inventor: Jörgen Holmén, Uppsala (SE)

(73) Assignee: PHACOTREAT AB, Uppsala (SE)

( * ) Notice: Subject to any disclaimer, the term of this patent is extended or adjusted under 35 U.S.C. 154(b) by 371 days.

This patent is subject to a terminal disclaimer.

(21) Appl. No.: 10/162,268

(22) Filed: Jun. 3, 2002

(65) Prior Publication Data

US 2003/0014021 A1 Jan. 16, 2003

Related U.S. Application Data

(63) Continuation-in-part of application No. 09/848,784, filed on May 3, 2001, now Pat. No. 6,533,769.

(51) Int. Cl.
*A61M 31/00* (2006.01)
*A61B 19/00* (2006.01)
*A61F 2/16* (2006.01)

(52) U.S. Cl. .................. 604/521; 128/898; 623/6.56
(58) Field of Classification Search ............. 604/506, 604/521; 128/898; 623/4.1, 6.11, 6.56; 435/183; 514/2
See application file for complete search history.

(56) References Cited

U.S. PATENT DOCUMENTS

| | | | |
|---|---|---|---|
| 4,909,784 A | 3/1990 | Dubroff | 604/49 |
| 5,013,295 A | 5/1991 | Dubroff | 604/38 |
| 5,188,590 A | 2/1993 | Dubroff | 604/22 |
| 5,204,331 A | 4/1993 | Nishi et al. | 514/54 |
| 5,375,611 A | 12/1994 | Lindqvist et al. | 128/898 |
| 5,445,636 A | 8/1995 | Bretton | 606/41 |
| 5,616,122 A | 4/1997 | Lam et al. | 604/49 |
| 5,620,013 A | 4/1997 | Bretton | 128/898 |
| 5,651,783 A | 7/1997 | Reynard | 606/4 |
| 5,696,091 A | 12/1997 | York et al. | 517/12 |

(Continued)

FOREIGN PATENT DOCUMENTS

| | | |
|---|---|---|
| WO | WO 00/22459 | 4/2000 |
| WO | WO 01/77197 A3 | 10/2001 |
| WO | WO 01/77197 A2 | 10/2001 |

OTHER PUBLICATIONS

Gwon et al., "Restoring lens capsule integrity enhances lens regeneration in New Zealand albino rabbits," Refract Surgery, vol. 19, Nov. 1993, pp. 735–746.

*Primary Examiner*—Nicholas D. Lucchesi
*Assistant Examiner*—Mark K. Han
(74) *Attorney, Agent, or Firm*—Jenkens & Gilchrist, P.C.

(57) ABSTRACT

The invention relates to a method of performing ocular surgery, after an anterior capsulotomy has been made, by forming a sealed expanded capsular bag. The method includes sealing the capsular bag with a viscoelastic material to provide a gas tight seal to prevent leakage into the anterior chamber of the eye during the surgical process; expanding the capsular bag by introducing a gas capable of exerting a pressure on the inner surface of the capsular bag wall; inspecting and/or treating the capsular bag with one or several devices and/or agents suitable for performing inspection and/or treatment. The inspection and/or treatment can comprise any of visual inspection, estimation of capsular bag volume; labeling any residual epithelial cells to detect the presence thereof; removing residual epithelial cells, implanting one or more intracapsular implants; injecting a lens forming material for molding a lens in situ; drying the lens capsule; alone or in any combination. Use of a viscoelastic compound for the preparation of a temporary intraocular seal capable of sealing the capsular bag is also provided.

35 Claims, 11 Drawing Sheets

U.S. PATENT DOCUMENTS

| | | | |
|---|---|---|---|
| 5,760,075 A | 6/1998 | Stjernschantz et al. | 514/530 |
| 5,773,472 A | 6/1998 | Stjernschantz et al. | 514/530 |
| 5,792,099 A | 8/1998 | DeCamp et al. | 604/51 |
| 5,885,279 A | 3/1999 | Bretton | 606/41 |
| 5,972,889 A | 10/1999 | Courtois | 514/12 |
| 6,027,531 A | 2/2000 | Tassignon | 623/6 |
| 6,074,358 A | 6/2000 | Andrew et al. | 604/28 |
| 6,089,234 A | 7/2000 | Bretton | 128/898 |
| 6,186,148 B1 | 2/2001 | Okada | 128/898 |
| 6,254,587 B1 | 7/2001 | Christ et al. | 604/521 |
| 6,261,321 B1 | 7/2001 | Kellan | 623/6.51 |
| 6,319,222 B1 | 11/2001 | Andrew et al. | 604/28 |
| 6,358,279 B1 | 3/2002 | Tahi et al. | 623/4.1 |
| 6,367,480 B1 | 4/2002 | Coroneo | 128/898 |
| 6,533,769 B2 * | 3/2003 | Holmen | 604/521 |

* cited by examiner

METHODS AND COMPOSITIONS USABLE IN CATARACT SURGERY

PRIOR RELATED APPLICATIONS

This application is a continuation-in-part of application Ser. No. 09/848,784 filed on May 3, 2001, U.S. Pat. No. 6,533,769.

FIELD OF THE INVENTION

The present invention relates generally to cataract surgery (i.e. lensectomy), and more specifically to methods and compositions for treatments inside the lens capsule, preferably directed to treat lens epithelial cells, and methods of providing intraocular implants into the lens capsule, preferably injectable intraocular lenses molded inside the lens capsule, by the use of an ophthalmic composition of sodium hyaluronate with a specifically defined molecular mass and concentration.

BACKGROUND OF THE INVENTION

The crystalline lens of the human eye is located in the posterior chamber between the posterior iris surface and the vitreous body It is a biconvex transparent tissue without nerves and blood vessels, weighing approximately 0.2 g. The lens is enveloped in a capsule, a structureless, transparent and elastic membrane bag. Approximately 80 zonular fibers, extending between the capsule and the ciliary body, suspend the lens. The inside of the lens capsule consists of lens epithelial cells and lens fibers. The lens epithelial cells form a monolayer underlying the capsule from the anterior pole to the equator of the lens. These cells continue to undergo cell mitosis throughout life in the area located between the anterior pole and the lens equator The lens epithelial cells that underwent cell mitosis gradually move toward the lens equator and differentiate into lens fibers. These cells make up the rest of the lens. New layers of fiber cells are constantly formed on top of those previously formed The older fiber cells become denser and during the $3^{rd}$ decade of life a hard nucleus is formed in the middle of the human lens, consisting of old dehydrated fiber cells.

A cataract is defined as every form of opacity in the lens or its capsule; the lens becomes cloudy, resulting in a loss of visual ability A cataract is a painless phenomenon, but decreases the quality of life if the lens is not surgically extracted and replaced by an artificial lens.

When the lens is surgically extracted, an incision is made in the anterior part of the eye, i.e., the cornea or the sclera Then, a viscoelastic material is usually introduced into the anterior chamber to maintain the anterior chamber depth during surgery. An opening is made in the lens capsule by a procedure called capsulorhexis.

Following capsulorhexis, the lens is removed according to one of two principles: extracapsular cataract extraction (ECCE)—the cataractous lens is squeezed out through an opening in the anterior lens capsule and then removed through a 10–12 mm corneal incision, or phacoemulsification—the cataractous lens is dissolved with a special instrument, phaco-probe, by high frequency sonification and rinsed out through a 3–4 mm corneal incision.

Remaining parts of the lens, i.e. lens fibers and lens epithelial cells, are then removed using an irrigation and aspiration device After complete removal of the lens, the lens capsule is filled with a viscoelastic material and an artificial lens is implanted into it. Alternatively, a lens can be molded inside the lens capsule, as disclosed in PCT/EP99/07780. Thereby a cross-linkable polymer is injected into a lens capsule, and the lens is formed in situ. Another method for the same purpose but employing other materials is disclosed in PCT/EP01/04010.

Dyeing of the anterior lens capsule has been used to facilitate capsulorhexis in advanced/white cataract, to enhance critical steps during phacoemulsification and to perform capsulorhexis of the posterior lens capsule. Earlier studies have evaluated dyes, such as crystal violet, fluorescein, and indocyanine green, for dyeing the anterior lens capsule. Some dyes are applied by injection under the anterior surface of the capsule. Others are applied by a certain technique in which the anterior chamber is filled by gas, and the dye is applied on top of the anterior surface of the capsule. After a while, the dye is washed away by irrigation/aspiration and the anterior chamber is filled by a viscoelastic solution followed by capsulorhexis.

After cataract surgery, the most common postoperative complication is posterior capsule opacification (PCO) which has the clinical and economic significance to be considered as an important public health problem. Studies report that the incidence of PCO is ranging from 20% to 40% after approximately 4 years after surgery Migration and proliferation of remaining lens epithelial cells is the main cause of PCO. These cells grow from the peripheral parts of the capsule onto the posterior capsule and continue toward the axial region. Impaired visual acuity is the result caused by cell migration, proliferation and aggregation, the production of extracellular matrix, fibrosis and wrinkling of the lens capsule.

In the current clinical standard, patients who develop PCO are treated symptomatically by YAG laser capsulotomy. In this procedure a YAG laser disrupts the opacified lens capsule and the visual axis is cleared. However, YAG laser capsulotomy exposes patients to the risk of complications that can lead to severe visual impairment or loss of vision, such as retinal detachment, pupillary block glaucoma and cystoid macular edema Other complications associated with YAG laser capsulotomy include damage to implanted intraocular lenses resulting in glare and photophobia, dislocation of intraocular lenses, iritis, vitritis, corneal edema, iris damage and rupture of the anterior hyaloid.

From an economic point of view, symptomatic treatment of PCO is ranked one of the highest of the medical costs in the U.S.A. Thus, development of a procedure to prevent PCO reduces the medical costs related to YAG laser capsulotomy, including the costs for the treatment, its complications, and YAG laser equipment. Accordingly, there is a great need for PCO prophylaxis.

Mechanical and pharmaceutical methods for PCO prophylaxis by removing or destroying residual lens epithelial cells have been developed. However, none of them has been proved to be practical, effective, and safe enough for routine clinical practice.

Capsular polishing, aspiration of residual lens epithelial cells, ultrasound combined with aspiration, cryocoagulation, and osmolysis are examples of methods that have been developed and shown to remove or destroy remaining lens epithelial cells, but none of these methods have been proven to be efficient in PCO prophylaxis.

The design of the artificial intraocular lenses (IOL), such as the shape, size and materials of the IOL implanted during cataract surgery has also been shown to affect the development of PCO. It has been shown that a sharp bend in the capsule, created by a capsule tension ring or an IOL with sharp optic edges, may induce contact inhibition of lens epithelial cell migration on the capsule.

Various anti-metabolites such as doxorubicin, methotrexate, mitomycin, daunomycin/daunorubicin, 5-fluorouracil, colchicines and taxol are effective in inhibiting lens epithelial cells proliferation in vitro. However, in vivo animal studies have shown that there are toxic side effects in the tissues of the eye when anti-metabolites are used in sufficiently high concentration to inhibit lens epithelial cells proliferation. In attempts to avoid side effects on other ocular tissues an immunotoxin specifically inhibiting proliferation of lens epithelial cells has been evaluated. The anti-lens epithelial cell monoclonal antibody binds specifically to lens epithelial cells and carries ricin or saporin that kill proliferating cells. In the experimental studies, antibodies against human antitransferrin and FGF have been used as antibodies against lens epithelial cells. However, no conclusive results have been obtained Another pharmacological approach is to separate lens epithelial cells from the lens capsule. Ethylenediamine tetraacetic acid (EDTA) was included in an irrigation solution and a simulated extracapsular cataract extraction was performed to separate lens epithelial cells. In other attempts, EDTA was used with a viscoelastic material (U.S. Pat. No. 5,204,331 to Nishi et al., 1993), or simply introduced into the lens capsule. When an EDTA solution was included in an irrigation solution and a simulated extracapsular cataract extraction was performed in cadaver eyes, the anterior lens epithelial cells could be separated. EDTA seems not to be more efficient than other agents evaluated in PCO prophylaxis.

Enzymes such as trypsin and DISPOSE (protease) have also been evaluated for separation of lens epithelial cells. When a 2% trypsin solution was included in an irrigation solution and a simulated extracapsular cataract extraction was performed in cadaver eyes, lens epithelial cells were stripped in places. The cell separation was partially successful. However, the zonules were damaged by the trypsin solution. The use of an active enzyme can be a problem even when an enzyme solution is introduced into the lens capsule because it can damage the zonules bound to the lens capsule. According to U.S. Pat. No. 4,909,784 to Dubroff 1990, when a cell-killing substance is introduced into the lens capsule through a small hole, without first removing the lens, lens epithelial cells are killed. A drawback when using this method is that the efficacy of the treatment may be strongly limited, if the natural lens is not removed before administrating the cell-killing substance. The natural lens may absorb or decrease the efficacy of the substance due to the huge number of lens epithelial cells within the lens. A viscoelastic material that is introduced into the anterior chamber prevents the active agent from escaping from the lens capsule, and prevents damage to the corneal endothelium. In related patents (U.S. Pat. No. 4,909,784 to Dubroff 1990, U.S. Pat. No. 5,013,295 to Dubroff 1991), a syringe to remove the introduced substance from the lens capsule through a small hole was disclosed. However, physically and technically, it seems to be difficult to efficiently remove the substance introduced into the lens capsule before capsulorhexis without damaging the lens capsule. The remaining substance may escape from the lens capsule and damage the cells and tissues facing the anterior chamber during and after capsulorhexis.

An important problem in connection with all methods relating to cataract surgery is the difficulty of observing the interior of the lens capsule, especially behind the iris, in order to ascertain that measure taken were successful, such as the removal of residual lens epithelial cells.

U.S. Pat. No. 5,651,783 (Reynard 1995) discloses a fiber optic sleeve that permits endoscope visualization of intraocular structures either through the surgical handpiece or through an end piece attachment. However, this patent is silent in regard of evaluating the capsular inside in a turbulent flow of irrigation solution and lens materials flowing around the end of the fiber optic during the process of phacoemulsification and irrigation-aspiration, and such evaluation appears very difficult given the premises in the patent. Gwon et al, in *J. Refract. Surgery*, Vol. 19, November 1993, pp 735–746 discloses that the lens capsule was expanded with air and perfluoropropane by closing a capsulotomy of a size 2.5 to 3.5 mm with a patch, attached to the capsule by Healon and overlapping the capsule by at least 1 mm. The reason was to study the effect on lens regeneration in rabbits and cats Nothing was explained of using the technique in other aspects. Additionally, it seems difficult to use the technique of closing off the capsule with a patch for performing different procedures within the capsule, as the patch would block introduction of devices into the capsule and performance of different methods within the capsule. Furthermore, the authors describe the situation that the capsule is not completely filled by air, but a mixture of air and viscoelastic solution (Healon®).

SUMMARY OF THE INVENTION

In view of the problems and drawbacks associated with prior art methods it is an object of the present invention to provide methods and compositions that facilitates access to the interior of the capsule during intraocular surgery in general.

This object is achieved in a first general aspect of the invention by a method which comprises injecting gas for expanding the lens capsule, and sealing the capsule with a viscoelastic composition so as to enable maintaining it in an expanded state during a period of at least 10 seconds, while at the same time allowing access to the interior for the purpose of performing various operations therein, without the gas leaking out.

The method is defined in claim 1.

The present invention is based on the establishing of a sealed lens capsule by the use of an ophthalmic composition of sodium hyaluronate (i.e. viscoelastic solution) with a specifically defined molecular mass and concentration. The expression "sealed" or "sealing" is taken to mean that the capsule is essentially sealed against gas leakage or leakage of solutions out from the capsule, for a time sufficient to allow surgical intervention to be made, for example the implantation of devices, implants, gases and solutions to be moved into and out of the lens capsule. Thereby, it is enabled to introduce a gas into the lens capsule, to expand the capsule, and to maintain it expanded in such manner that devices, implants and agent solutions can be introduced into the gas expanded lens capsule, and procedures previously impossible to perform can be done inside the capsule. One of the main reasons is to avoid any damages to the delicate endothelial cells on the posterior surface of the cornea during the performance of different treatments/surgical techniques within the capsule.

The method according to the invention includes the benefits to use patches in combination with a viscoelastic solution for sealing the capsule to prevent leakage from the capsule, and on the same time allow entrance into the lens capsule for treatment of lens epithelial cells and performance of different procedures inside the lens capsule.

In one embodiment of the invention, using the general inventive concept above, the invention provides a method allowing safe elimination of proliferating lens epithelial cells during cataract surgery, thereby preventing the occurrence of PCO.

The treatment/administration may be performed as an extra step in routine cataract surgery. It is quick and easy to learn and perform for all cataract surgeons.

From an economic point of view, development of a procedure to prevent PCO reduces the medical costs related to YAG laser capsulotomy, including the costs for the treatment, its complications, and YAG laser equipment.

As the active agent is administered locally on the inner surface of the lens capsule in a very efficient way, the required dose of the active agent is very low. The active agent is distributed completely over the entire interior surface of the capsule by the phenomenon of surface tension. Thereby, the active agent will be administrated specifically to the lens epithelial cells, and distribution to other delicate cells within the eye, e.g. the corneal endothelial cells, is prevented. The gas filled environment also ensures that the concentration of the administered active agent solution is maintained, since the irrigation solution has been removed from the capsule and no effect of dilution will be present.

The method described in this patent application comprises the benefits of a removed lens during the local treatment of the lens capsule (compare with method according to U.S. Pat. No. 4,909,784 to Dubroff 1990, wherein the lens is not removed before treatment). Since the lens is never in contact with the active agents, diminished absorption or activity of the agents is prevented. This ensures that distribution over the whole capsule can be accomplished with an active agent solution of low concentration that will be minimally diluted or diffused into adjacent sensitive tissues.

The treatment/administration of the capsule may also be performed even if an IOL has been implanted, for example at initial indications of PCO development directly after or up to several years after the cataract surgery.

Implantation of Devices into the Lens Capsule

In another embodiment of the invention, implantation of different devices is enabled and facilitated into the gas expanded lens capsule A gas expanded capsule makes an implantation safe and predictable. Examples of devices to be implanted are 1) patches (compare with implantation of a patch according to Gwon et al, in *J. Refract. Surgery*, Vol. 19, November 1993, pp 735–746, wherein the capsule is not expanded at the time of implantation of a patch),
2) intraocular lenses (compare with standard implantation of intraocular lenses, wherein the capsule is expanded by a viscoelastic solution), see FIG. 9 which illustrates introduction of an ordinary IOL,
3) valves (compare with U.S. Pat. No. 6,358,279 to Tahi et al. 2000, wherein the natural crystalline lens is not removed before the valve is put in place),
4) capsular rings
5) any other kind of device to be implanted into the lens capsule.

Volume and Size Estimation of the Capsule

In a further embodiment of the invention, estimation of the capsule interior volume is enabled. This is of great value before implantation of injectable intraocular lenses molded in the lens capsule. By knowing the lens capsule volume, the amount of lens fluid material required to mold a lens inside the capsule can be estimated before the implantation process is initiated. Thereby, overfilling or incompletely filling the capsule with the lens fluid solution is prevented Thus, the refractive properties of a molded intraocular lens can be successfully achieved. The volume is estimated by injecting gas into the capsular bag; measuring the amount of gas injected; measuring the intra ocular pressure in the capsular bag; and calculating a volume using said measured values.

Drying and Cleaning of the Lens Capsule

For all the above described procedures it is beneficial to dry and clean the lens capsule interior surface. By this optional but highly preferred procedure, any undesired remaining solution inside the lens capsule can be removed, e.g. viscoelastic solutions, agent solutions, irrigation solutions. The procedure involves removing solutions out of the gas expanded lens capsule by devices having absorbing or suction capabilities, or by evaporating solutions with a continuous gas flow into and out of the gas expanded lens capsule. The capsule should preferably remain expanded during the process of drying.

A dry and clean capsule, achieved by removal of solutions, is of great value before treatments within the lens capsule, e.g. treatment of lens epithelial cells by agent solutions Thus, the agent solution is not diluted and the whole interior lens capsule surface is exposed to the treatment. Thereby, an efficient treatment is achieved.

The dry and clean capsule also enhance inspection inside the capsule by fiber optics, by means of visualizing the interior capsule surface without any disturbing solutions, such as viscoelastic solutions, agent solutions and irrigation solutions.

Furthermore, a dried capsule ensures attachment of patches within the lens capsule to seal or close a capsulotomy. The dry environment enables attachment of patches to the capsule by an adhesive material, preferable for permanent attachment using a glue. The attachment will be improved by the avoidance of surfaces covered by solutions.

In addition, the effect of drying and cleaning is of great value before implanting injectable intraocular lenses molded inside the lens capsule. Remaining solutions inside the lens capsule have potential to impair the formation of the surface and the form of an intraocular lens molded inside the lens capsule by causing artifacts to the lens. Thus, a dry and clean interior lens capsule surface avoid such negative influence, and thereby secure that the lens will receive desired refractive properties.

Inspection Within the Lens Capsule

Another preferred and optional procedure that can be carried out in the invention in connection with any or all of the above described procedures, is inspection of the lens capsule interior surface for identifying artifacts, injuries, remaining lens epithelial cells etc. It was surprisingly found that such inspection was enabled and facilitated by the gas expanded lens capsule (compare with U.S. Pat. No. 5,651, 783 to Reynard 1995, wherein inspection is performed during a turbulent flow of irrigation solution during phacoemulsification and irrigation-aspiration which seems to impair the visual outcome).

The inspection is easily performed by using fiber optics, or an ordinary surgical microscope. The fiber optics gives the advantage of enabling inspection of hidden sections of the capsule behind the iris, incomplete dilated pupils in particular.

Inspection has an important medical value before/after a directed treatment within the capsule, to check the conditions before a treatment, and to evaluate the result of such treatment, e.g. detection of remaining lens epithelial cells, preferable marked by a dye or signal substance specifically detecting the cells of interest.

Additionally, it has a great medical value to inspect the lens capsule before implantation of an injectable intraocular lens to be molded inside the lens capsule. An intact lens capsule, e.g. no injuries of the capsule, should be guaranteed to avoid leakage of injected lens fluid material. Any other artifacts that should be compensated for, before or during the process of molding, can be successfully identified.

Mold of an Intraocular Lens

In still another embodiment of the invention there is also provided an improved method of molding an intraocular lens in vivo, by virtue of the inventive sealing procedure.

The process of molding is improved by the use of a gas expanded capsule.

The three steps, described below, can be used separately, or used together partly, or as a sequence to form a desired shape of the anterior surface of an intraocular lens at the molding process.

First, the lens capsule can be formed into a desired shape by filling the anterior chamber with different portions of viscoelastic solution 13 with desired rheologic properties in specific regions 26 of the anterior capsule to exert a specific pressure onto the anterior part of the gas expanded lens capsule. On the same time the IOP and the volume inside the gas expanded capsule can be adjusted for to achieve the desired form and volume of the capsule before injecting a lens forming fluid. Preferable, the refractive power in the mold-gas situation should be controlled simultaneously by suitable equipment.

Second, the gas can be proportionally exchanged with a lens forming fluid to keep the desired form of the lens capsule during the process of injecting and molding an intraocular lens.

Third, the anterior surface of the injected intraocular lens, and thereby the refractive properties of the lens, can be adjusted for by removing or injecting viscoelastic solution within the anterior chamber before or at the time of the hardening process of the lens fluid material. Localized placement of viscoelastic material in different positions within the anterior chamber will exert different formation capabilities of the lens's anterior surface. Viscoelastic solutions with different rheologic properties will exert different positioned conformation ability on the surface, i.e. high viscosity will cause a more focused pressure onto the lens's surface than a low viscosity viscoelastic solution. The viscosity of the viscoelastic solution is preferably chosen to fit the viscosity of the lens forming fluid. The viscoelastic solution mold should have a higher viscosity than the lens forming fluid to secure the form of the mold. However, localized injected viscoelastic solutions into the anterior chamber mold may have less viscosity than the lens forming fluid.

Temporary Intraocular Seal

In a further aspect of the invention, there is provided use of a viscoelastic material for making a temporary intraocular seal capable of sealing a gas expanded capsular bag during a surgical process involving lensectomy, and in another aspect there is provided use of a viscoelastic material for making a temporary intraocular mold useful for forming a lens implant from a fluid material injected into the capsular bag.

BRIEF DESCRIPTION OF THE DRAWINGS

The present invention will now become more fully understood from the detailed description given herein, wherein reference is made to the accompanying drawings, in which.

DETAILED DESCRIPTION OF EMBODIMENTS
OF THE PRESENT INVENTION

As already indicated, the basic idea behind the novel methods in cataract surgery according to the present invention, is to employ a gas to expand the lens capsule and to maintain it in expanded condition such that procedures previously impossible or at least difficult to perform can be done.

Thus, below several methods employing this basic inventive idea will be described and exemplified.

First, a standard procedure for the removal of the lens 10 is illustrated with reference to FIGS. 1–2.

A general methodology employing gas will be described, and several methods employing this basic inventive methodology will be described and exemplified.

However, first a standard procedure for the removal of the lens 10 is illustrated with reference to FIGS. 1–2.

Figure 1:
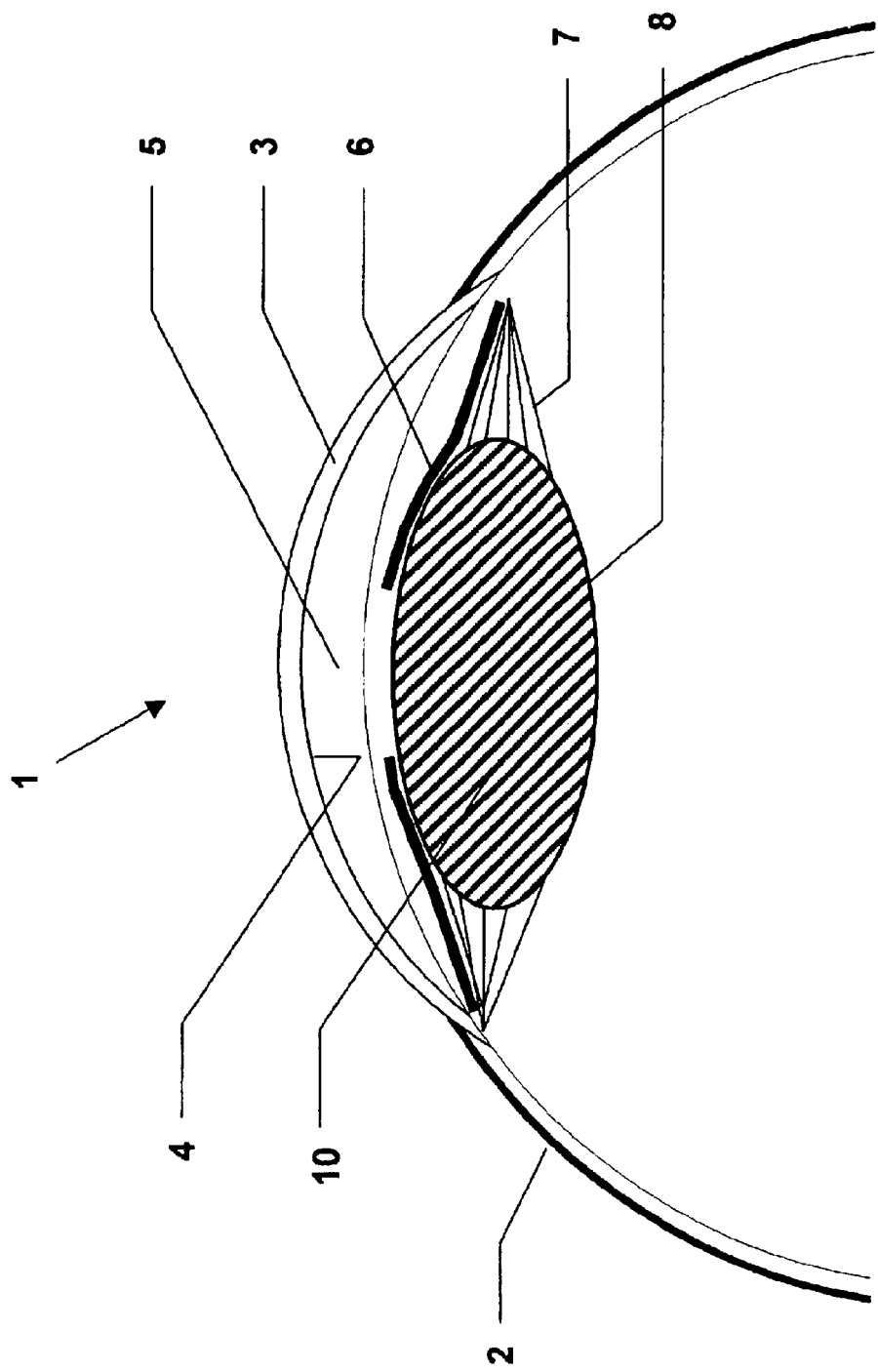
FIG. 1 shows a cross-sectional view of the human eye before surgery.
Figure 2:
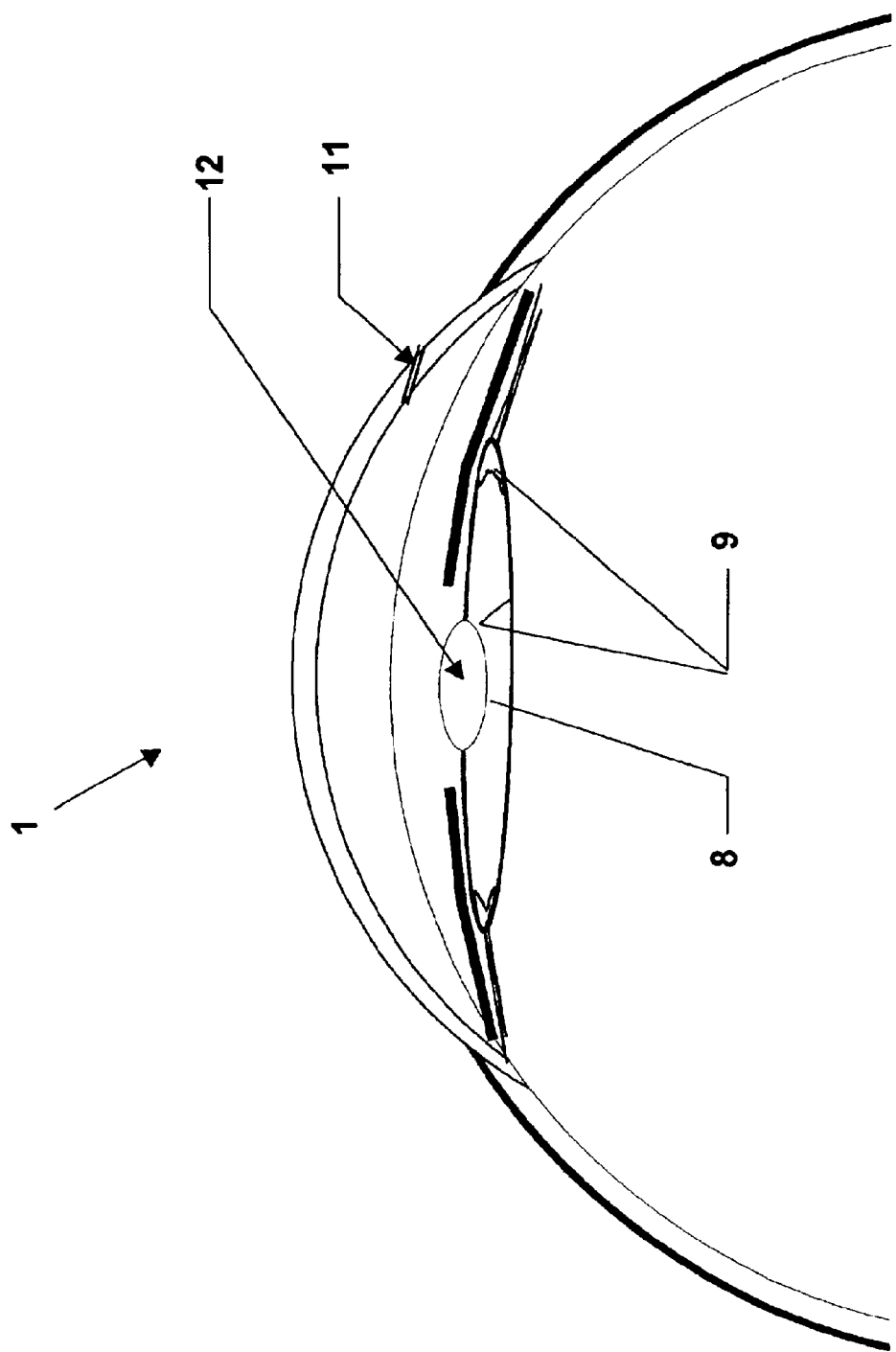
FIG. 2 shows a cross-sectional view of the human eye after lens extraction.

FIG. 1 schematically illustrates a human eye 1.

In the surgical extraction of the lens 10, an incision is made in the anterior part of the eye, in the cornea or the sclera 3. Then, a viscoelastic material 13 is introduced into the anterior chamber 5 to maintain the anterior chamber depth. An opening (capsulorhexis) 12 is made in the lens capsule 8.

Following capsulorhexis, the lens 10 is removed according to phacoemulsification—the cataractous lens 10 is dissolved with a phaco-probe by high frequency sonification and rinsed out through a 3–4 mm corneal incision 11.

Reference Numbers 6 and 7 Designate the Iris and the Zonular Fibers, Respectively The method according to the present invention will now be illustrated with reference to FIGS. 3–7.

Figure 3:
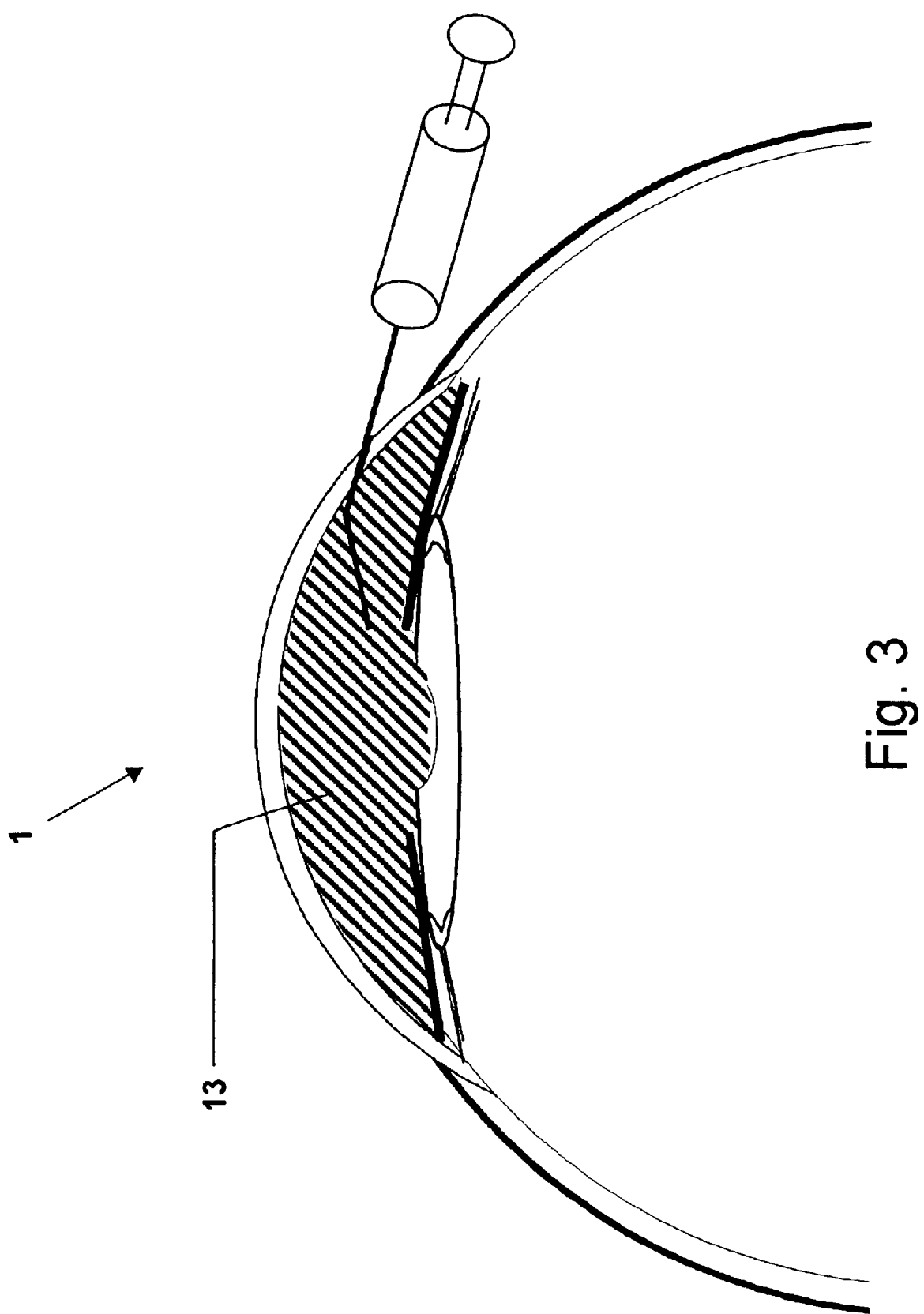
FIG. 3 shows a cross-sectional view of the human eye after injection of viscoelastic substance into the anterior chamber.

When the lens 10 is removed, a viscoelastic solution 13 or equivalent solution is injected into the anterior chamber 5 (see FIG. 3).

The viscoelastic solution 13 should have certain Theological properties in order to confine the gas 14 (to be injected, see FIG. 4) within the lens capsule 8, thus effectively providing a sealing of the lens capsule A suitable substance is Healon5 (Pharmacia AB, Uppsala, Sweden) or similar viscoelastic solution. The viscoelastic solution 13 might be such that it has the ability to eliminate the toxicity of any active agent 15 (to be introduced into the capsule) escaping from the lens capsule. Suitable viscoelastic compounds and their preparation are disclosed in WO 98/39015 (Pharmacia & Upjohn AB), specifically in Examples 1 and 2 presented in that patent. This publication is incorporated in its entirety herein by reference. Another commercially available compound suitable for the purpose is Microvisc® Phaco (Bohus Biotech AB, Strömstad, Sweden).

Figure 4:
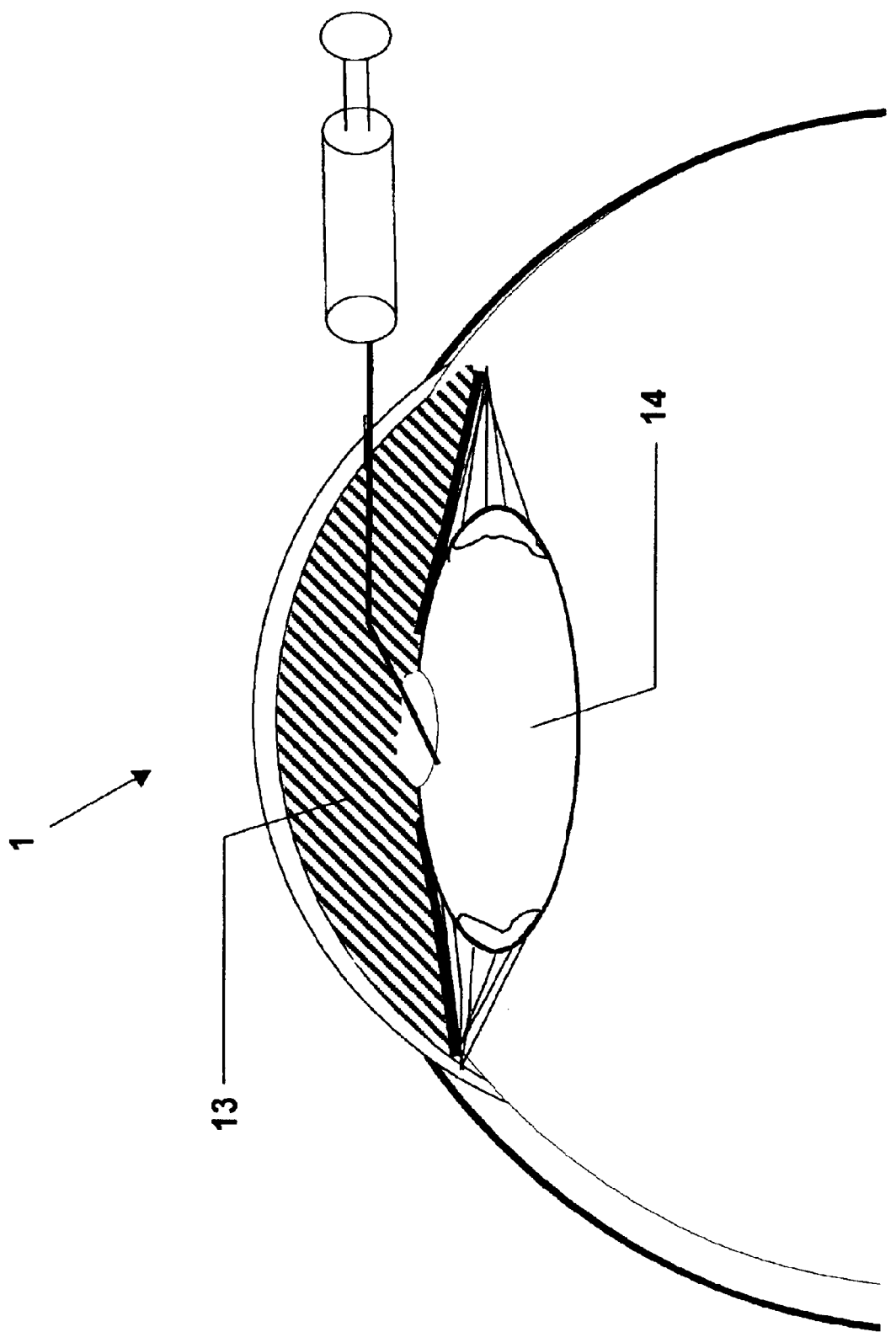
FIG. 4 shows a cross-sectional view of the human eye after injection of gas into the lens capsule.
Figure 5:
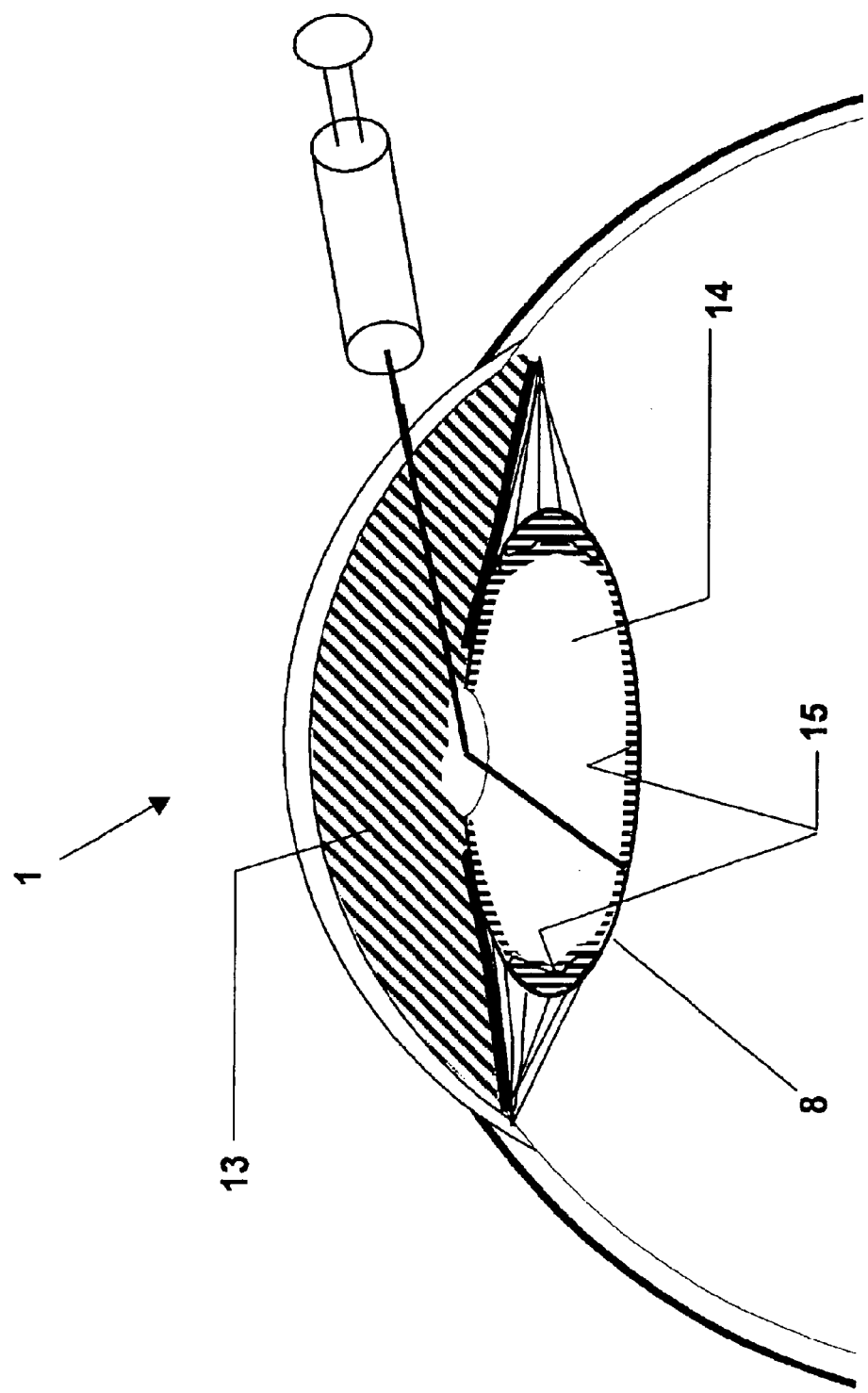
FIG. 5 shows a cross-sectional view of the human eye after application of an active agent within the lens capsule.
Figure 6:
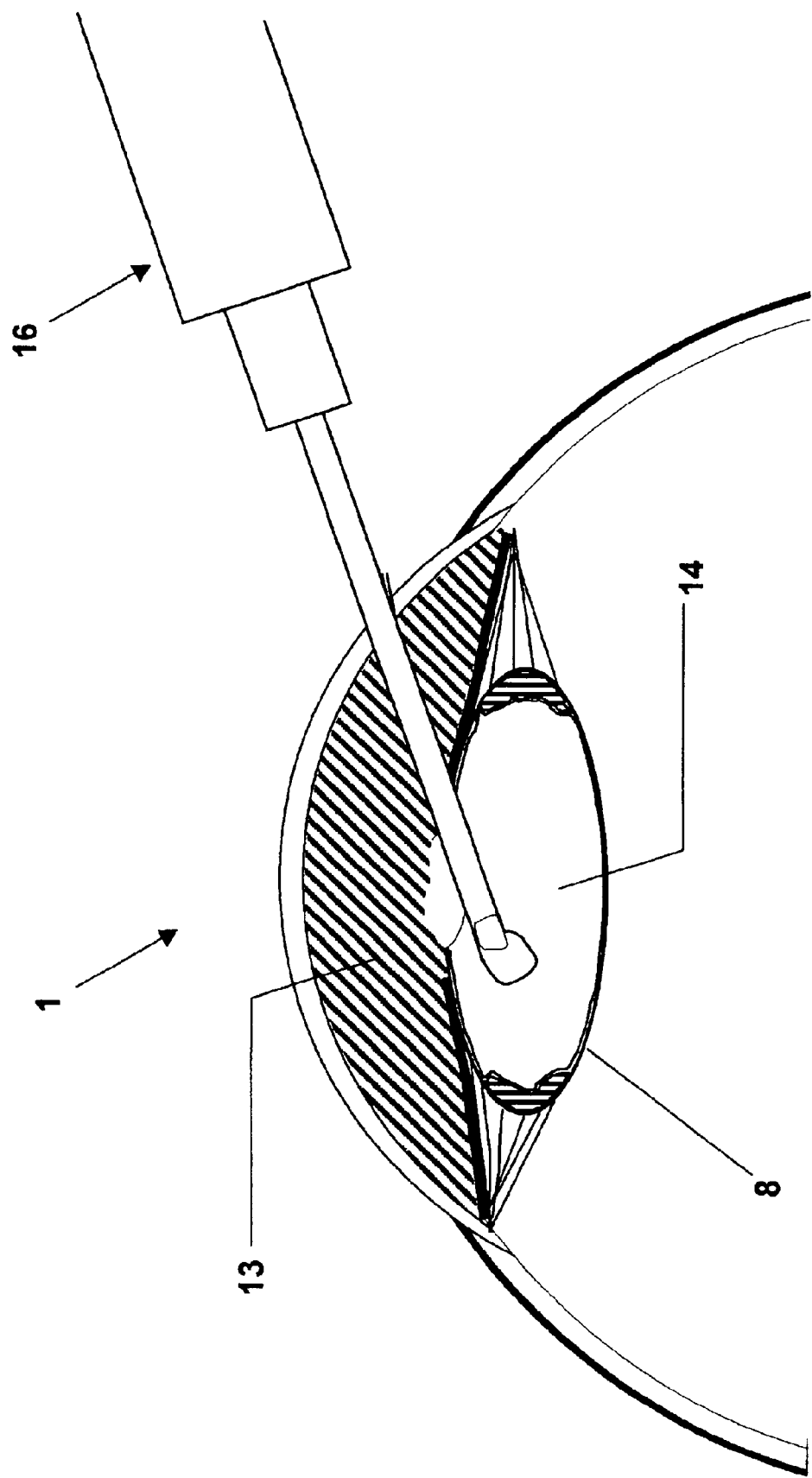
FIG. 6 shows a cross-sectional view of the human eye during irrigation and aspiration within the lens capsule.
Figure 7:
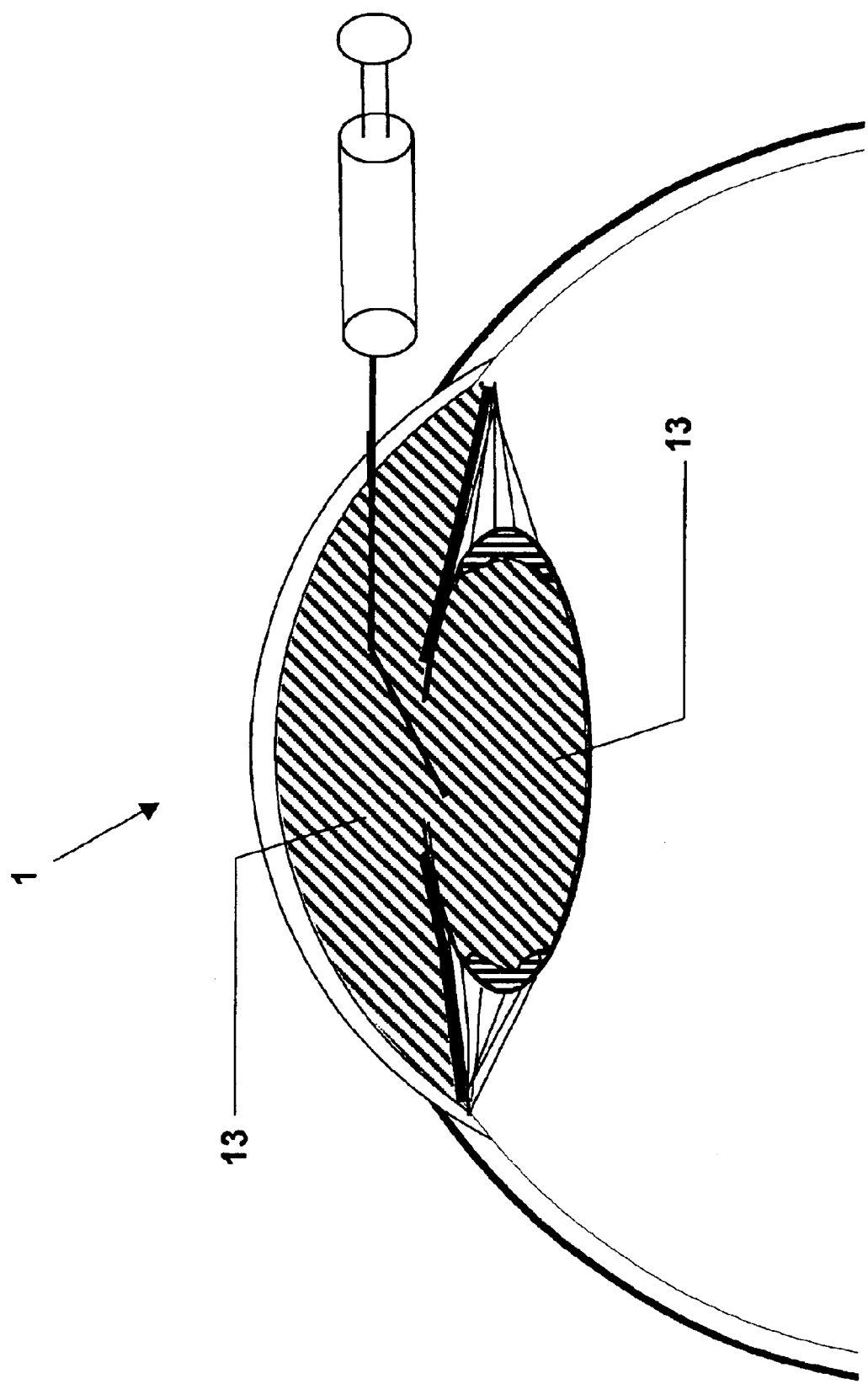
FIG. 7 shows a cross-sectional view of the human eye after injection of viscoelastic substance into the lens capsule

When the viscoelastic solution 13 is in position, a gas 14 is injected into the lens capsule 8, whereby the gas is confined by the pressure of the viscoelastic solution 13 (see FIG. 4). The gas is injected to keep the lens capsule 8 expanded during manipulations performed inside the lens capsule, such as administration of an active agent (e.g. active to kill epithelial cells, although other active agents are possible too), cleaning, drying, removing lens residues etc.

Preferably, the gas 14 should not be reactive to tissues within the eye that which are not to be treated. The gas should not be reactive with water, i.e. create acidic or alkaline conditions. Instead, preferably it should be inert. The gas is preferable clear and/or invisible. It preferably comprises air, i.e., approximately 78% nitrogen and 21% oxygen.

The gas may be the active agent 15. The gas should then have the same effect on lens epithelial cells as the active agents described below.

Subsequent to the injection of the gas 14, an active agent solution 15 is injected onto the inner surface of the lens capsule 8. Due to the gas-expanded lens capsule 8, the administration of the active agent 15 becomes local and very efficient (see FIG. 5).

When injecting the agent solution, it is critical to avoid leakage at the moment of removing the device of agent application from the eye. Leakage may happen out of the gas-filled capsule, through the channel created when the device of application is removed from the viscoelastic solution in the anterior chamber, and through the corneal incision. This has been identified by the colored agent solutions in different experiments performed. To avoid the above described phenomenon, the following parameters should be properly adjusted for:
1. The intraocular pressure within the gas-filled capsule should be kept as low as possible, e.g at 15 mm Hg or lower, at the time of agent solution application, only high enough intraocular pressure to fulfil the requirement of an expanded capsule.
2. The tip of the applicator should be touched to the surface of the interior capsular wall to remove remaining solution attached to the tip.
3. The amount of agent solution applied to the capsule surface should be kept as small as possible, about 0.05 ml or less.
4. The tip of the device should be made suitable to avoid leakage.
5. The anterior chamber should be homogeneously filled with a highly viscous viscoelastic solution (e.g Healon5 or Microvisc phaco), i.e. the viscoelastic solutions should not be mixed with any irrigation solution or equivalent, to assure an efficient seal of the capsule.
6. It is of great advantage to refill the anterior chamber (e.g. exchange existing viscoelastic solution) with a fresh viscoelastic solution, if any other operations have been performed within the eye before the step of treating the capsule by an active agent solution.
7. When removing the device for application of the agent solution, the tip should not be removed straight out of the capsule and the anterior chamber. Instead, the tip should be moved upwards and waved within the viscoelastic solution in the anterior chamber to make sure that no channel is left behind the device in the viscoelastic solution. Thereby, no channel is present and the leakage is prevented.

In one embodiment of the invention, the active agent solution contains one or more agents with toxicity to lens epithelial cells 9 (see FIG. 1). The method according to the invention prevents diffusion of the active agent to other parts of the eye. The concentration of the active agent should be such that it exerts the necessary effect but nothing more. Examples of possible active agents are doxorubicin, indomethacin, EDTA, 5-fluorouracil (5-FU), FGF-saporin, methotrexate, mitomycin, daunomycin/daunorubicin, colchicines and taxol, although any other active agent giving the desired effect is usable in the inventive method Another method to be used to remove the lens epithelial cells with the invented gas filled capsule is by photodynamic treatment (PDT) of the lens epithelial cells. An example is given by using green porphyrin according to U.S. Pat. No. 6,248,734 to Meadows et al. Jun. 19, 2001, filed Mar. 27, 2000 (Use of photodynamic therapy for prevention of secondary cataracts).

The active agent solution is preferably dyed to encourage safe and complete removal of the drug when the treatment is terminated The dye should have equivalent or higher diffusion rate within viscoelastic solutions compared to the active agent. Then, the active agent does not reach to the corneal endothelial cells 4 (see FIG. 1) before the dye does, which can be observed in the surgical microscope. Examples of dyes are trypan blue, fluorescein.

An alternative would be to use an active agent that is colored, e.g. trypan blue, or an active agent to which a dye has been bound, e.g. the dye fluorescein Diffusion of the active agent 15 from the lens capsule 8 to the surrounding viscoelastic solution 13 can easily be spotted because the active agent solution is colored. The dyed viscoelastic solution 13 can then be removed by for example an I/A-instrument 16. Diffusion of active agents to other parts of the eye can thus be prevented.

The administration of the active agent can also be followed by the addition of a second active agent, which have the ability to prevent or slow down further proliferation of lens epithelial cells 9 that might have survived the exposure to the first agent. The second active agent may be administered at the same time as the first one. It may also be so that only one active agent, having the properties of both the first and the second active agent, is administered.

The local treatment by the active agent 15 is performed for a specific time. Its duration has to be long enough to (irreversibly) damage or kill the lens epithelial cells 9. To prevent diffusion to other delicate tissues, this time should not be made longer than necessary The removal or inactivation of the active agent is performed by using an I/A-instrument 16 (see FIG. 6). It is a standard device used in surgical operations in the eye having an irrigation and aspiration ability. Mild settings have to be used with the I/A-instrument 16 to prevent the viscoelastic solution 13 within the anterior chamber 5 from being removed.

Before removal of the active agent by an I/A-instrument, the active agent may be inactivated by another agent, that may be administered in a similar way as the active agent, i.e. by application onto the inner surface of the gas-filled capsule.

Injection of a viscoelastic solution 13 into the lens capsule 8 (see FIG. 7) may be used to enhance implantation of an IOL or prevent contact between the treated area and other tissues. The viscoelastic solution may contain a substance that inactivates the toxic agent. The viscoelastic solution might be the same as being used in the anterior chamber.

The lens capsule 8 has to be intact and a proper capsulorhexis has to be created before using the described method. The method starts after complete removal of the cataractous lens by using for example phacoemulsification. The treatment comprises the steps of (please refer to FIGS. 2–6).

a) filling anterior chamber 5 with a viscoelastic solution 13 (Healon5 or a similar solution with similar Theological properties),
b) injecting gas (e.g. air, nitrogen, perfluoropropane) 14 into the lens capsule 8, whereby the gas confined by the pressure of the viscoelastic solution 13, in order to maintain the depth of the anterior chamber 5 and to avoid dilution of the active agent solution 15,
c) injecting a colored solution of the active agent 15 within the gas-filled area of the lens capsule 8, whereby the color indicates the distribution of the active agent 15, which helps to prevent displacement,
d) the active agent solution 15 is removed from the gas-filled capsule 11 by irrigation and aspiration using an I/A-instrument 16, or inactivated by another agent administered into the capsule.

An IOL can be implanted after a previously performed lensectomy in an eye. Thus, a foldable intraocular lens can be implanted as follows:
1) The anterior chamber is filled with a viscoelastic solution (e.g fluorescein labeled Healon5 or Microvisc Phaco)
2) A gas is injected into the lens capsule to expand the volume of the capsule
3) A folded IOL is introduced into the gas expanded capsule by a pair of forceps or an IOL injector and unfolded within the gas expanded lens capsule.

The surgery can then proceed by removing the viscoelastic from the anterior chamber to finish the surgery.

Remaining viscoelastic solution is avoided behind the implanted IOL, evaluated by Scheimpflug photography which would show any remnants of labeled viscoelastic solution behind IOLs.

Another type of implant is so called capsular rings. These can be implanted after a previously performed lensectomy in an eye as follows:
1) The anterior chamber is filled with a viscoelastic solution (e.g. Healon5 or Microvisc Phaco).
2) A gas is injected into the lens capsule to expand the volume of the capsule.
3) An extended capsular ring is introduced into the gas expanded capsule and placed within the gas expanded lens capsule.

The surgery can then proceed by removing the viscoelastic from the anterior chamber to finalize the surgery.

The method according to the present invention described above will be illustrated with reference to the non-limiting examples 1–3, given below.

Inspection of the inside of the lens capsule for artifacts, injuries etc. is enabled and facilitated within the expanded lens capsule. Inspection has an important medical value before/after a directed treatment within the capsule or before an injection of an lens forming fluid into the lens capsule to avoid leakage. The inspection is easily performed by using fiber optics, or an ordinary surgical microscope The fiber optics gives the advantage of enabling inspection of hidden sections of the capsule behind the iris, especially in small pupil surgery.

In order to improve the knowledge of the orientation in the image received by the fiber optics from the capsule, it is preferred to use a reference marker at the end of the fiber optics that is identified in the images received. By knowing the position of the reference marker of the fiber optic device the surgeon is informed about which part of the capsule is displayed in the image. A graded hairline showed in the image of the capsule make it easier for the surgeon to estimate distances within the capsule.

Furthermore, the above described method of inspection of an expanded capsule make it possible to identify remnants of lens epithelial cells. The remnants of cells is spotted by the use of fiber optics or an ordinary surgical microscope or other usable equipment for localizing marked/labeled cells. The demand of resolution is lower than for the visual inspection of the capsule.

The detection of cells is improved by labeling the cells within the gas expanded capsule with a dye, a fluorescent substance or a specific marker for lens epithelial cells with a signal structure (molecule, enzyme, substance etc.) attached to it. The signal structure can be identified by a reaction that will reveal the prevalence of the identified cells or that the signal structure can be identified directly, e.g. a dye, a fluoresce substance. The detection of cells is preferably made by the same equipment as for the inspection of the capsule inside.

Figure 10:
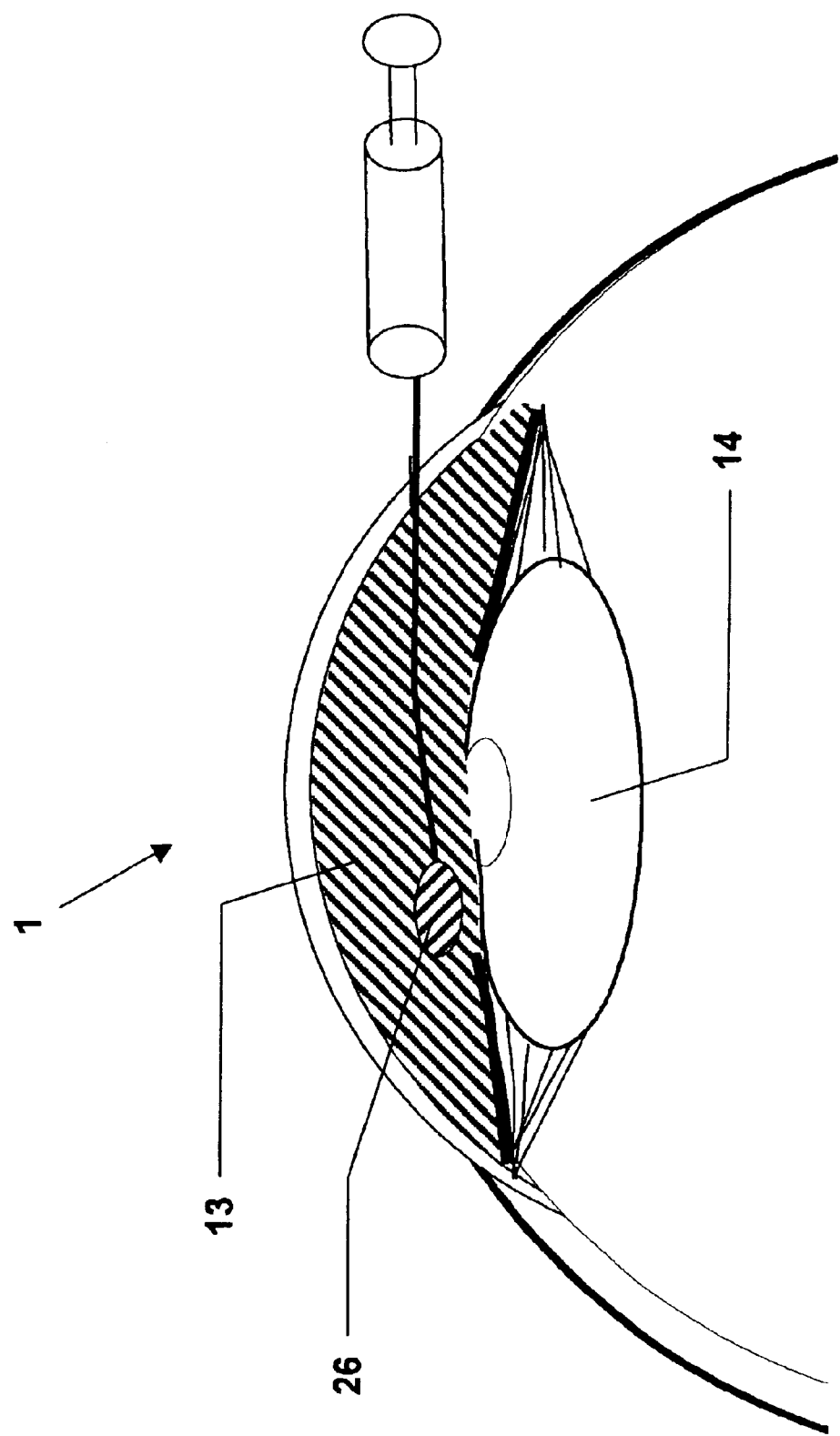
FIG. 10 illustrates a locally placed amount of viscoelastic solution to achieve a local pressure on the anterior lens capsule and thereby induce a change in the desired anterior chamber mold to be used for molding a lens forming fluid into a intraocular lens implant
Figure 11:
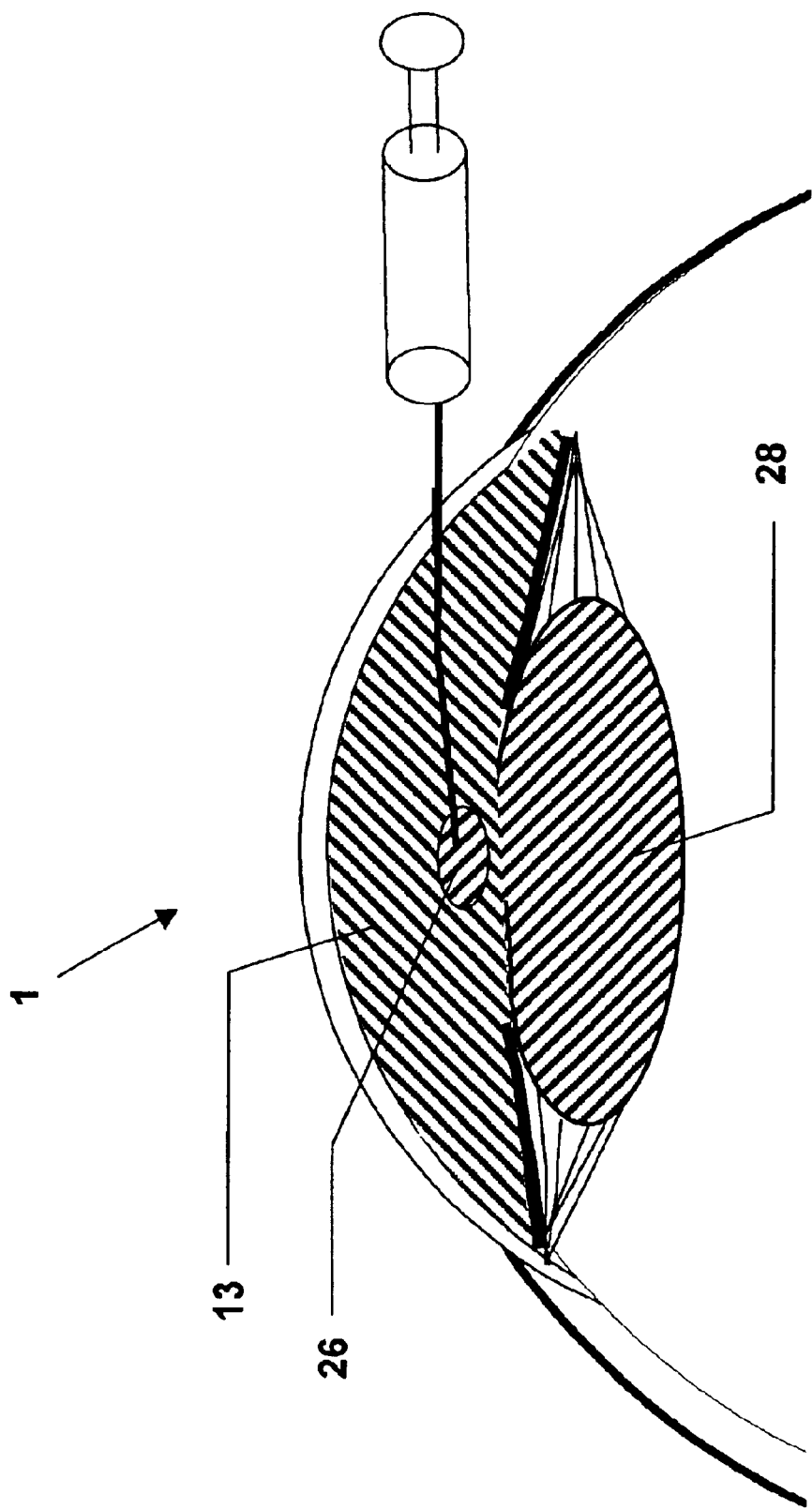
FIG. 11 illustrates a locally placed amount of viscoelastic solution to achieve a local pressure on the anterior lens capsule, and thereby induce a change in refraction of the lens forming fluid during the process of molding an intraocular lens implant.

In a further aspect of the invention, there is provided a novel method of molding an intraocular cell in vivo, which is improved over prior art methods by virtue of the inventive sealing procedure in combination with the expansion using gas (reference is made to FIGS. 10–11).

Thus, visual correction of an eye is performed by forming an intraocular lens in the capsular bag from which the natural crystalline lens has been surgical excised. The method includes as a first step sealing the capsular bag by introducing a sufficient amount of a sealable viscoelastic material 13 into the anterior chamber of the eye. Then a predetermined amount of a lens forming fluid 28 is injected into the capsular bag (FIG. 11). More viscoelastic material may be locally introduced 26 into the anterior chamber in an amount sufficient to affect the shape of the anterior surface of the capsular bag 8. Optionally, the visual outcome of the eye is controlled, and if necessary, said viscoelastic material is locally reintroduced in manner so as to approach a desired visual outcome. The final lens implant is formed inside the capsular bag.

It is also possible to fill the lens capsule 8 with gas and to perform the procedure of shaping the capsule before injecting the lens forming fluid (FIG. 10).

Preferably, the lens forming fluid comprises a silicone material having a specific gravity that is greater than 1.0 and a refractive index of a natural lens that is polymerized from a plurality of siloxane monomers. The refractive index preferably ranges between 1.383 and 1.695, and at least one siloxane monomer has a specific gravity greater than 1.0. More preferably the silicone is a terpolymer having a specific gravity of about 1.1 and a refractive index of about 1.41. Alternatively, the silicone is a copolymer having a specific gravity of about 1.1 and a refractive index of about 1.41.

Figure 8:
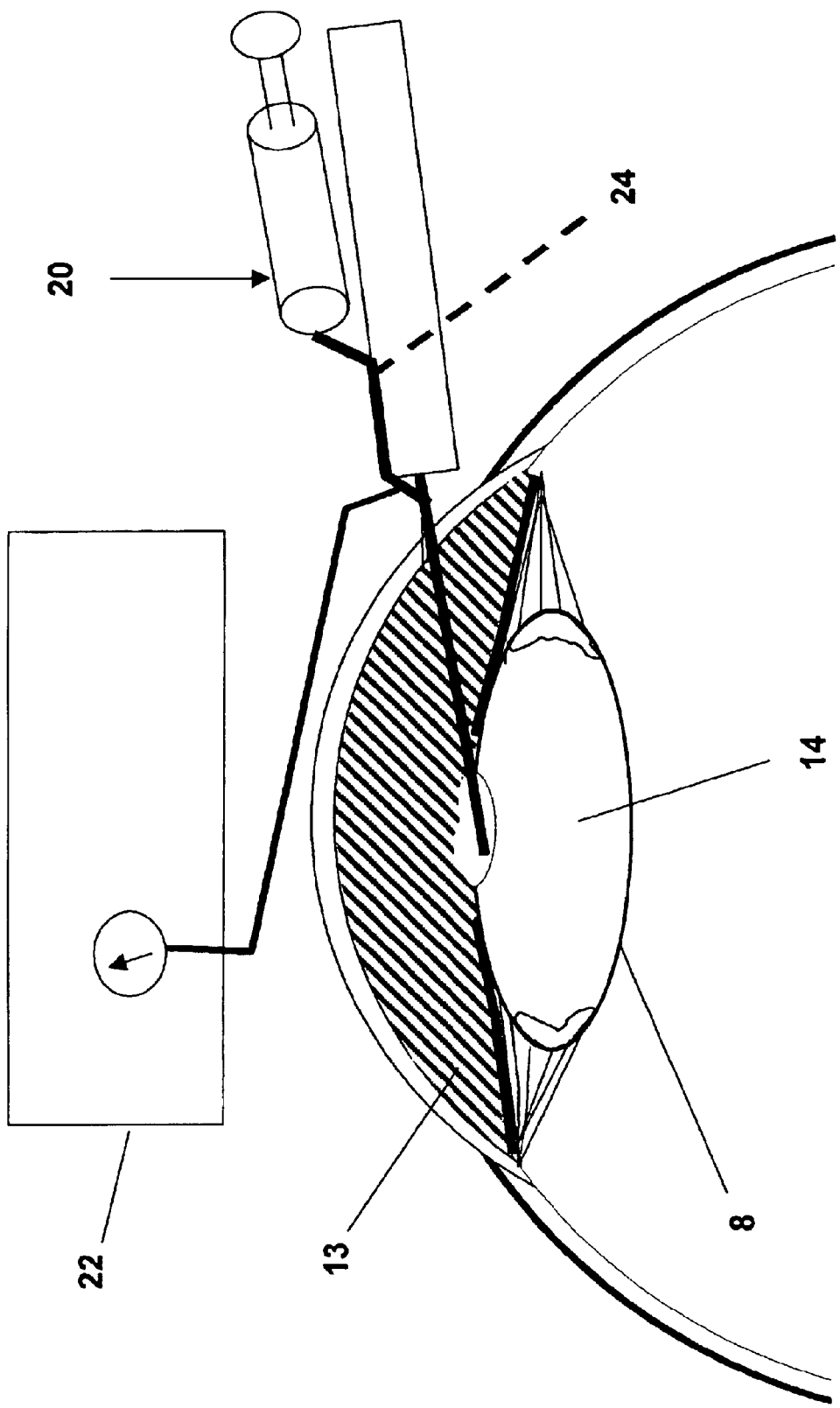
FIG. 8 illustrates IOP/volume estimation of lens capsule.

Suitable materials and their preparation are disclosed in WO 00/22459 (Pharmacia & Upjohn AB), in Examples 1–6 therein, and WO 01/77197 (Pharmacia Groningen BV). Methods of implantation are disclosed in Examples 7–8 in said publication, which is incorporated herein in its entirety by reference Before molding an intraocular lens implant in the lens capsule, it is important to know the volume of the capsule to estimate the amount of lens material that should be injected. The method of filling the capsule with a gas enables such measurements, by estimation of the gas volume injected, Intra Ocular Pressure (IOP), flow rate etc, schematically illustrated in FIG. 8 (see also Example 4).

Thus, after a previous performed lensectomy in an eye, the following procedure is performed in order to estimate the volume:

1) The anterior chamber is filled with a viscoelastic solution 13 (Healon5 or Microvisc Phaco).
2) The lens capsule is filled with a gas (e.g. air, nitrogen, perfluoropropane) and the volume injected is estimated by a graded scale onto the injection device 20 (e.g. a syringe), thereby the volume of the capsule was estimated. The volume of gas correlates to the volume and the size of the lens capsule The sealed capsule guarantees that no gas leaks out of the capsule at the moment of volume estimation
3) The surgery can now proceeded with various operations.

In an embodiment, the method described above is performed simultaneously with measurement of the IOP during the gas injection, using a pressure gauge 22 coupled to the injection device When the IOP reaches a specific level (e.g. 10, 15, 20 mmHg) the volume of the capsule is estimated by the volume of gas injected, as described above The advantage is that overfilling of the capsule by gas is avoided, and that it can be ascertained that the capsule is completely filled by gas.

It is also possible to simultaneously measure gas flow rate during the gas injection with a suitable flow meter 24. By also measuring the time of injection at specific flow rates, the volume of the capsule can be estimated.

Furthermore, it is also possible to simultaneously measure the IOP during the gas injection. When the IOP reaches a specific level (e.g. 10, 15, 20 mmHg) the volume of the capsule is estimated, similarly as described above.

In a further variation, the flow rate is kept constant during the gas injection. The period of time during the gas injection is estimated until the capsule is filled up. The volume of the capsule can then be calculated It is also of importance to be able to control the IOP within the capsule at the performance of different methods within the gas expanded capsule to increase safety, e.g. a higher pressure in the capsule than necessary during a directed treatment do increase the risk of leakage of substances from the capsule. The gas expansion of the capsule enables pre-shaping the lens capsule before a lens forming fluid is injected into the capsule (see Example 5).

In a still further aspect there is provided a method of performing ocular surgery, after an anterior capsulotomy has been made, by forming a sealed expanded capsular bag in accordance with the procedures outlined above. The surgical method includes sealing the capsular bag with a viscoelastic material to prevent from leakage into the anterior chamber of the eye during the surgical process, in a manner as disclosed above. The capsular bag is expanded, by introducing a medium, suitably it is accomplished with a gas, an aerosol, or an aqueous fluid, preferably air or nitrogen or perfluoropropane, capable of exerting an equal pressure on the inner surface of the capsular bag wall. Then, the capsular bag is inspected and/or treated with one or several devices suitable for performing such activities, such as fiber optics, cleaning equipment. Optionally the capsular bag is provided with an artificial implant. Preferably inspecting the capsular bag involves visual inspection and/or estimation of capsular bag volume.

The treatment suggested above preferably includes introduction of an agent into the capsular bag that is capable of preventing PCO from occurring, i.e having the effect of killing epithelial cells to prevent the proliferation If desired, the gas can be the active agent, but it can also be injected in form of a solution onto the inner surface of the gas-filled lens capsule. The active agent can be a colored active agent, or an active agent to which a dye has been bound The active agent can also be in a colored solution. The purpose of the colored agent is to stain the lens epithelial cells to render them more easily visible, and the combination of staining the cells and expanding the lens capsule with a gas is novel and inventive, in that the gas has an additive effect in the staining of the cells Other labeling techniques can also be used, e.g. antibody specific detection of residual lens epithelial cells, radioactivity, signal molecules, colors for other cell structures etc.

Thus, in accordance with the invention it is made possible to treat lens epithelial cells with cytotoxic substances, e.g. 5-fluorouracil, daunomycin or other substances toxic to the cells in combination with a gas that eliminates the side effects of toxicity to the corneal endothelium The gas combined with a cytotoxic agent will have additive effect, by increased efficacy and decreased toxicity to the corneal endothelium.

Other treatments that are made possible within the methodology provided by the invention are radioactive treatment by alfa-radiation; treatment with anti-neoplastic substances; treatment with anti-mitotic substances; treatment with cytotoxic substances (5-FU etc.).

The active agent, after having (irreversibly) damaged or killed the lens epithelial cells (9), is inactivated in or removed from the lens capsule (8).

In a further step the inner surface of the gas-filled lens capsule is coated with a second active agent, capable of preventing cell growth and migration onto the posterior region of the capsule for as long as possible, and the addition of the second active agent is preferably subsequent to the addition of the first active agent. Both the first and second active agents can also be administered at the same time.

Alternatively, an active agent is administered which have the properties of both the first and the second active agent.

The viscoelastic solution can be made to have the ability to eliminate the toxicity of the active agents, and/or the ability to prevent diffusion of the active agents to adjacent tissues Sometimes it will be desirable to repair the capsular bag, and the present invention in a further aspect provides a method to patch up an artifact/injury of a lens capsule. The method comprises the introduction of a thin membrane into the lens capsule, and attaching the membrane to the injured part of the lens capsule. Thereby, the interior capsule is mended. The reason for to patching up the capsule may be due to surgical failed capsulorhexis, removal of artifacts (opaque areas along the optic axis, mislead refraction along the optic axis etc.), or other reasons of capsular defects Another reason to patch up the capsule is to enable introduction of a lens forming fluid to mold an intraocular lens into an eye with a large capsulorhexis already made in the anterior or posterior surface of the capsule or both, e.g. capsulorhexis made at a former IOL implantation.

To enable accommodation of an intraocular lens molded in the capsule, the patching of larger openings of the capsule has to be made with a membrane attached more secured to the capsule with the use of an adhesive material, or a glue designed for use on tissues such as the lens capsule. The glue is preferably uncolored to secure the visual acuity at the optical axis. If colored, it is preferable that it is bleached over time A colored glue is otherwise to be preferred to display the placement of the glue before attaching the capsule patch implant. A colored glue is less of a problem when it is placed out of the optical axis. The seams of the glue/attachment is preferably situated away from the optical axis for light of vision focused onto the retina.

As mentioned above such repair involves surgically attaching a patch of a biocompatible material, which suitably can be collagen. The collagen can be bovine collagen Type I, III or IV (see Gwon et al, in *J. Refract. Surgery*, Vol. 19, November 1993, pp 735–746). In order to ensure a good closure, suitably a fibrin sealant is introduced to secure closure. An example of a suitable sealant is Tissucol®. To provide a secure closure it is also desirable that the patch is located over the anterior capsulotomy with an overlap of at least 1 mm.

After a previously performed lensectomy in an eye, the following is made to take care of an identified capsulotomy (i.e. hole in the lens capsule),
1) The anterior chamber is filled with a viscoelastic solution (Healon5 or Microvisc Phaco).
2) A gas is injected into the lens capsule to expand the volume of the capsule.
3) Glue (e.g. fibrin sealant, labeled by a dye or unlabeled, or Tissucol®) is attached to the capsule surrounding the capsulotomy.
4) A rolled-up patch (e.g. a thin collagen membrane or simulated by a piece of plastic) is introduced into the gas expanded capsule and unfolded.
5) The patch is placed over the capsulotomy to close it.

The surgery proceeds with other operations such as molding an intraocular lens.

After a previously performed lensectomy in an eye, the following is done to take care of an identified artifact (e.g. a light distorting part of the lens capsule),
1) The anterior chamber is filled with a viscoelastic solution (Healon5 or Microvisc Phaco).
2) A gas is injected into the lens capsule to expand the volume of the capsule.
3) The part of the capsule with the artifact is removed by a continuous curvilinear capsulorhexis.
4) Glue (e.g. dye labeled or unlabeled fibrin sealant or Tissucol®) is attached to the capsule surrounding the capsulotomy.
5) A rolled-up patch (e.g. a thin collagen membrane or simulated by a piece of plastic) is introduced into the gas expanded capsule and unfolded.
6) The patch is placed over the capsulotomy to close it.

The surgery proceeds with other operations, such as molding an intraocular lens.

Figure 9:
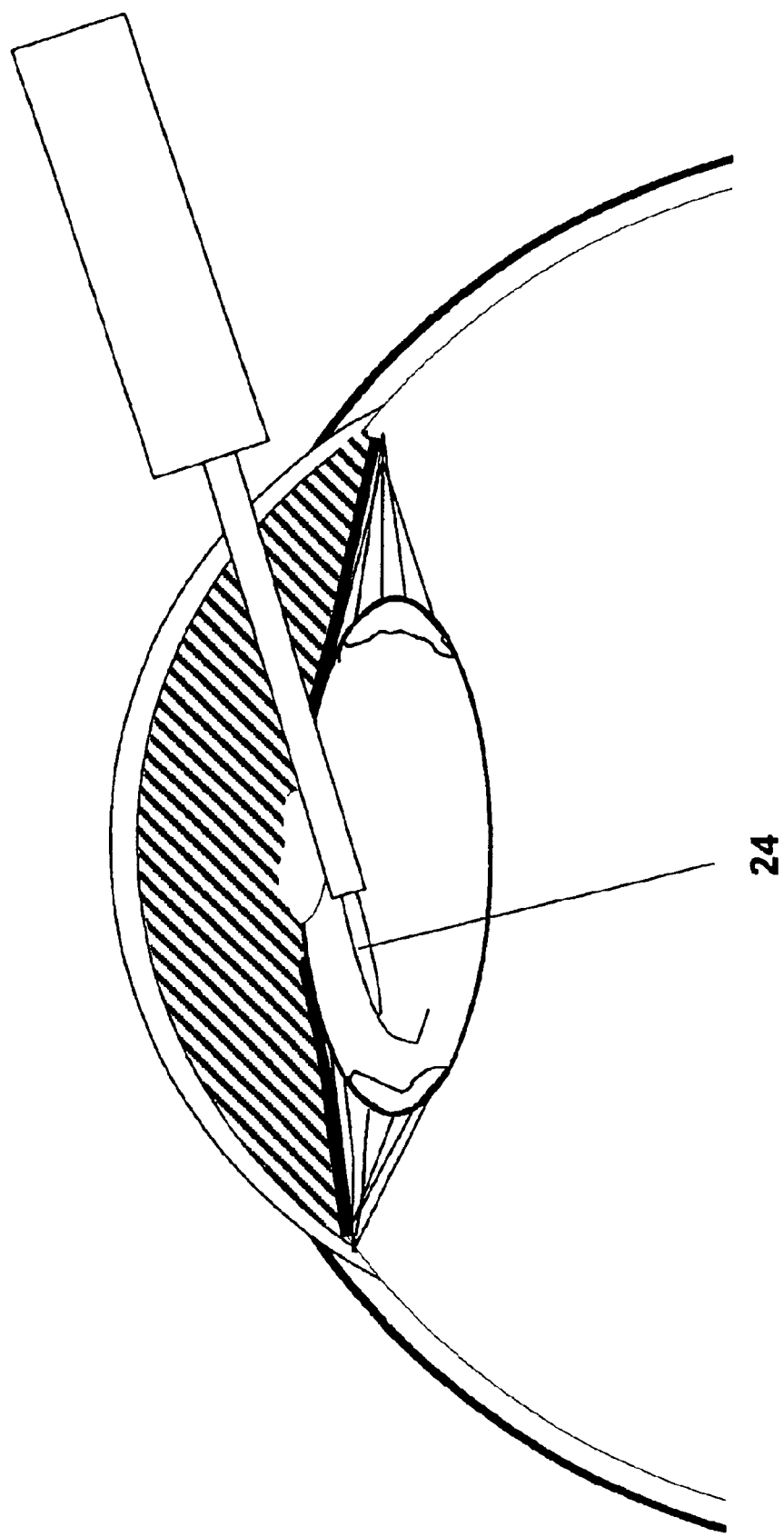
FIG. 9 illustrates implantation of valves, patches, ocular rings, IOLs, capsule molded IOLs.

In the above procedures a treatment against PCO can be performed before the procedures begin.

Where the natural crystalline lens has been surgically excised including the formation of a capsulorhexis, said capsulorhexis is preferably sealed with a plug that admits entrance into the capsular bag For the purpose of making a lens in situ, a lens forming fluid is injected into the capsular bag The treatment of the capsular bag described above may include inserting an applicator charged with an agent capable of preventing from PCO. If it is desirable, the method can include insertion of an ordinary intraocular lens implant comprising an optical part and haptics capable of securing said implant in the capsular bag (see FIG. 9).

It has been discovered that a viscoelastic solution in combination with a valve at the lens capsule opening constitute an additional advantage to maintain a gas and different agents within a gas expanded capsule. The valve is preferably designed to be used to close the capsule after injection of a lens forming fluid to mold an intraocular lens. A method has been invented to attach a valve at a capsulorhexis from the inside of a gas expanded lens capsule. The gas expanded capsule admits to place a valve implant at the lens capsular opening from the inside of the capsule in a dry environment, e.g. micro capsular opening at implantation of a lens forming fluid to mold an intraocular lens. The method for implantation is preferably performed similar to attachment of capsule patch implants, as previously described. An example of a prior art valve suitable for use with the present invention is disclosed in U.S. Pat. No. 6,358,279 (Tahi).

After a previously performed lensectomy in an eye a mini capsulorhexis valve is implanted by following procedure,
1) The anterior chamber is filled with a viscoelastic solution (e.g. Healon5 or Microvisc Phaco).
2) A gas is injected into the lens capsule to expand the volume of the capsule.
3) A mini capsulorhexis valve is introduced into the gas expanded capsule and placed at the capsulorhexis of the gas expanded lens capsule.

The surgery proceeds by different operations (e.g. molding of an intraocular lens).

A further requirement is to implant specific devices in a dry environment and a dry interior capsule surface, e.g. to attach implants to the capsule more securely, such as lens patch implants, capsulorhexis valves and intraocular lenses molded in the capsule. A method to dry the interior capsule surface comprises drying the surface of the gas expanded lens capsule by a device with solution suction capability, e.g. capillary suction, or by a continuous flow of gas into and out of the capsule to evaporate any remaining solution All of the above discussed procedures can be combined in optional ways, such that the cataract surgeon will have a versatile and efficient methodology available for enhancing the quality of the surgery, and also to enable more rapid procedures to be performed In still a further aspect of the invention a viscoelastic aqueous composition of a polysaccharide with both dispersive and cohesive qualities is used for the preparation of a temporary intraocular seal capable of sealing a gas expanded capsular bag during a surgical process involving lensectomy for a time sufficient to admit inspection of the capsular bag inside and to treat the capsular bag to prevent from posterior capsule opacification Cohesive and dispersive properties of viscoelastic solutions, as well as the Theological characteristics of Healon5 is described by Dick, H. B. and Schwenn, O. in the book "Viscoelastics in Ophthalmic Surgery" Springer-Verlag Berlin Heidelberg, Germany 2000.

Said composition has a concentration within the range of 18–40 mg/ml sodium hyaluronate and the sodium hyaluronate having a molecular mass within the range of $2.5 \times 10^6$ to $10 \times 10^6 < M >_{r,M}$. Preferably the molecular mass of the sodium hyaluronate is within the range $2.5. \times 10^6 - 6 \times 10^6 < M >_{r,M}$ and the concentration of the aqueous solution is within the range of 18–35 mg/ml. Most preferably the molecular mass of the sodium hyaluronate is within the range $2.5 \times 10^6 - 5 \times 10^6 < M >_{r,M}$ and the concentration of the aqueous solution is within the range of 20–28 mg/ml The composition may further comprise a compound acting as a scavenger.

In a still further aspect, a viscoelastic composition defined as above is used for the preparation of a temporary intraocular mold, useful for forming a lens implant from a fluid material injected into the capsular bag by exerting a sufficient controlled adjustable localized pressure on the anterior surface of an expanded capsular bag in order to obtain a shape controlled molding of the anterior surface of a final lens implant and thereby obtain a controlled refractive outcome of treated eye.

Now the pre-shaping of lens capsule, by an anterior chamber mold of a viscoelastic solution (gas imprint) will be described.

After a previously performed lensectomy in an eye, the following procedure is performed:
1) The anterior chamber is filled with a viscoelastic solution (Healon5).
2) A gas is injected into the lens capsule to expand the volume of the capsule. Thereby, an imprint is formed of the expanded capsule into the viscoelastic solution.
3) By regulating the gas volume in the capsule and/or the IOP, and on the same time adding or removing viscoelastic solution in the anterior chamber, the shape of the anterior surface of the lens capsule is adjusted to yield differences in the refraction rate.
4) When the gas is removed from the capsule the imprint of the anterior capsule surface remains in the viscoelastic solution.
5) When a lens forming fluid is injected into the lens capsule for molding an intraocular lens, the anterior surface of the lens capsule is positioned into the same shape as the imprint in the viscoelastic solution. By this, it is possible to control the refraction of the anterior surface of the lens forming fluid in the process of molding an intraocular lens. The procedure is followed by Scheimpflug photography using an EAS-1000 instrument.

It is also possible to simultaneously as the lens forming fluid is injected remove the gas, i.e. the IOP remains relatively stable during the procedure. Thus, the form of the capsule (i.e. the anterior chamber mold of viscoelastic solution, e.g. Healon5) is kept secured during the procedure of injecting the lens forming fluid into the gas expanded capsule, thereby the imprint in the viscoelastic solution remains intact.

The anterior chamber can be molded to form a molded lens (lens forming fluid) in the following manner:

After previous performed lensectomy in an eye,
1) The anterior chamber is filled by a viscoelastic solution (Healon5).
2) A lens forming fluid is injected into the lens capsule (simulated by fluorescein labeled Healon).
3) The shape of the anterior lens capsule is adjusted to yield a specific desired refraction pattern by filling and removing viscoelastic solution from the anterior chamber. A highly viscous viscoelastic solution (e.g. Healon5) locally placed at a specific position in the anterior chamber will induce a local specific change in the shape of the anterior capsule, and thereby also the lens implant. Thereby, a local change of refraction is yielded in the molded lens. A less viscous viscoelastic solution (e.g. Healon) will yield a more gentle change in the shape of the anterior capsule and a different change in the refraction of the molded lens.

The outcome of this procedure to make local adjustments of the molded lens implant makes it possible to correct for local refractive disorders, e.g. corneal astigmatism (the procedure is monitored by the use of EAS-1000 produced Scheimpflug photographs).

In an alternative embodiment, essentially the same procedure is followed, besides that the IOP is controlled in the process of adjusting the shape of the anterior capsule, i.e. the molded lens anterior surface, by viscoelastic solutions.

In the forming of an imprint into the viscoelastic solution by the gas expanded capsule, it is furthermore possible to perform the step of adjusting the shape of the lens capsule in the process of molding the lens implant as disclosed above.

Preferably, in the process of the molding of a lens, a specific amount of lens forming fluid is used, said volume being estimated by a capsular volume estimation.

Preferred viscoelastics to be used with the present invention will have Theological properties as outlined, in an article by Harding et al, in *Carbohydrate Polymers*, 47 (2002) 109–119, for hyaluronan solutions with concentrations above 15–17 mg/l and Mw above $3.2 \times 10^6$. The invention will now be illustrated by way of non-limiting examples.

EXAMPLES

Example 1

Evaluation of a Preferred Embodiment of the Invention

Cataract surgery was simulated in porcine cadaver eyes An eye was fixed on a plastic holder while maintaining a standardized intraocular pressure of 10–15 mm Hg before surgery. Further details of the model are published elsewhere (Holmen J B, Ekesten B & Lundgren B (2001) Anterior chamber depth estimation by Scheimpflug photography. Acta Ophthalmol Scand Vol. 79:576–579.) The example was performed as follows:
1) A corneal incision 11 was performed at the limbus of the cornea 3.
2) The anterior chamber 5 was filled with a viscoelastic solution 13 (Healon5, Pharmacia AB, Uppsala, Sweden) by injection.
3) A continuous circular capsulorhexis was created.
4) Phacoemulsification was performed by an anterior segment operating system (Oertli Quinto, Oertli Instrumente A G, Berneck, Switzerland) with complete removal of the cataractous lens 10.
5) Additional viscoelastic solution 13 (Healon5) was injected into the anterior chamber 5.
6) The lens capsule 8 was filled with a gas 14 (78% nitrogen, 21% oxygen, 1% argon, i.e. fresh air) by injection.
7) An active agent solution 15 (fluorescein 10 $\mu$l/ml, no active agent) was applied onto the inner surface of the lens capsule 8, and distribution over the inner surface of capsule was noted.
8) A period of incubation, adjusted to be sufficient for dyeing the capsule 11, i.e. simulation of treatment of lens epithelial cells 9 by an active agent 15.
9) The active agent solution 15 was removed by irrigation and aspiration within the lens capsule 8 without removing the viscoelastic solution 13 in the anterior chamber 5
10) Viscoelastic solution 13 in which the dye is diffused within is then removed in the same way.
11) The lens capsule 8 is filled by a viscoelastic solution 13.

The efficiency of the inventive administration was evaluated visually in the surgical microscope, by slit lamp photography and by dissection. The photos and the dissected parts were examined visually with respect to distribution and leakage of the test solution.

During the phase of gentle injection of the colored test solution into the gas-filled capsule 8 the solution was distributed all over its inner surface, as being observed in the surgical microscope.

No leakage of the colored substance through the capsulorhexis, i.e into the anterior chamber, was observed.

Photos taken after application also showed that the capsule was colored and that there was no leakage. The same was found when dissecting the lens capsule.

In conclusion, the example indicates that the inventive method administers a small amount of solution efficiently, that is, the treating solution is selectively distributed on the aimed surface. The method also prevents diffusion of the active agent to other not targeted tissues.

Example 2

Example 2 was performed using the method described in Example 1, except for using trypan blue instead of fluorescein in the agent solution. The distribution of the active agent solution 15 was studied by free preparation of the lens capsule 8.
The results were equal to the ones in Example 1

Example 3

Example 3 is performed using the method described in Example 1, but using a plurality of known active substances in the agent solution, e.g. doxorubicin, EDTA, indomethacin, 5-fluorouracil (5-FU), FGF-saporin, methotrexate, mitomycin, colchicine or daunomycin/daunorubicin.

Example 4

Measurement of Volume

A gas is injected into the capsule. The volume of the injected gas is measured at the injection by, for example, a graded scale onto the device of gas injection (e.g. a syringe) The IOP is estimated by a pressure gauge connected to the device of gas injection. At a specific IOP or within an interval of IOP the injection of gas is stopped and the volume of the injected gas is estimated The volume of gas correlates to the volume and the size of the lens capsule.

Example 5

Pre-Shaping of the Lens Capsule

By expanding the capsule with a gas, the lens capsule will be pressed to the viscoelastic solution within the anterior chamber and form an imprint of the expanded capsule into the viscoelastic solution. By regulating the IOP within the capsule, and on the same time add or remove viscoelastic solution in the anterior chamber, the shape of the anterior surface of the lens capsule can be adjusted to yield differences in the refraction rate. When the gas is removed from the capsule the imprint of the anterior capsule surface will remain in the viscoelastic solution. When a specific amount of lens material is injected into the lens capsule for molding an intraocular lens, the anterior surface of the lens capsule will be positioned into the same shape as in the pre-shaping gas expansion to the imprint in the viscoelastic solution. By this, it is possible to control the refraction of the anterior surface of an intraocular lens in the process of molding.

Example 6

Patching a Lens Capsule

First, it is preferred that any other treatment to eliminate or remove residual lens epithelial cells have been performed before this procedure. Then, gas is introduced into the capsule and expand the volume (if not already done). An artifact of the lens capsule is dissected away by cutting or equivalent method for removing the artifact, i.e. a capsulorhexis is made. Glue is introduced and attached to the capsule around the capsulorhexis. A thin membrane is introduced into the lens capsule, e.g. a membrane rolled up and "injected" into the capsule. The membrane is unrolled and attached at the capsule to seal the capsulorhexis. The membrane is fixated onto the capsule by the glue or equivalent adhesive material or attachment principle.

Example 7

Capsule Volume Estimation and Molding of an Intraocular Lens Implant

A fresh cadaver eye from a newly slaughtered pig (Farmek, Uppsala, Sweden) was used in this experiment to simulate a cataract surgical procedure including capsule volume estimation and simulated molding of an intraocular lens implant. The eye was maintained in ice-cooled balanced salt solution (BSS®, Alcon Laboratories Inc, Texas, USA) until usage. Hypromellos (Isopto®-Plain, 5 mg/ml, Alcon Laboratories Inc., Puurs, Belgium) was applied topically to rinse the ocular surface and prevent the cornea from drying during the surgery.

The total surgical time is given in brackets after the step number, including the time for the surgical step.

Experimental Surgical Performance

1. A porcine cadaver eye was tempered to body temperature (37° C.).
2. The eye was mounted in a plastic holder by a compress and an o-ring.
3. The IOP (intraocular pressure) was measured by a pneumatonometer (Mentor® Model 30 Classic, Mentor O&O, Inc., Norwell, Mass., U.S.A.) and adjusted by stretching—releasing the tightness of the compress and the o-ring until an IOP of 20 mmHg was received.
4. The eye was moved to an EAS-1000 instrument (NIDEK Co Ltd., Japan) and a slit-lamp photograph was taken according to the Scheimpflug principle. The anterior chamber depth was estimated to 2.40 mm (ACD BS) and the anterior lens surface curvature to 6.46 mm by the EAS-1000 analysis program.
5. (0 s) The eye was moved to the surgical microscope (Leica M840, Heerbrugg, Switzerland). A clear corneal incision was made close to the edge of limbus with a 3.2 mm angled slit-knife (Sharpoint®, Surgical Specialties Corp., Reading, U.S.A). The tunnel incision was about 2.0 mm in length through the cornea.
6. (40 s) A viscoelastic solution with low viscous properties (Healon®, Pharmacia, Uppsala, Sweden), tempered to room-temperature, was injected into the anterior chamber through the incision, until first signs of anterior chamber overfilling was observed (i.e. leakage from the 3.2 mm incision). The amount of viscoelastic solution introduced into the anterior chamber was estimated by weight to 0.22 g (i.e. the difference in weight of the syringe, estimated before and after the injection, Wt A).
7. (160 s) The eye was moved from the surgical microscope to the EAS-1000 instrument and a slit-lamp photograph was taken. The anterior chamber depth was estimated to 2.44 mm (ACD Healon) and the anterior lens surface curvature to 6.49 mm by the EAS-1000 analysis program. The estimated ACD Healon was close to the previously estimated ACD BS. By this, the amount of injected viscoelastic solution was approximated to be equivalent to the volume of the anterior chamber before surgery, i.e. 0.22 ml.
8. (190 s) A continuous curvilinear capsulorhexis with a diameter of 4 mm was created on the anterior lens capsule by a pair of Corydon forceps (Moria, Paris, France). It was placed close to the iris at the corneal incision, reaching to the central region of the capsule.
9. (220 s) Approximately 0.5 ml balanced salt solution (BSS®) was injected between the lens capsule and the lens, thereby separating the capsule and the lens tissue (i.e hydro dissection).
10. (320 s) The lens was removed out of the capsule by phacoemulsification (i.e. high frequency ultrasound and continuous flow of irrigation solution (BSS®) and continuous aspiration) by an anterior segment operating system equipped with a peristaltic pump system (Oertli Quinto, Oertli Instrumente A G, Berneck, Switzerland; Setting of a vacuum of 150 mmHg, a flow of 25 ml/min, a bottle height of 70 cm, and <70% phaco power at the ultrasound frequency of 28 kHz)
11. Any remaining viscoelastic solution was removed from the anterior chamber by irrigation and aspiration simultaneously as the lens removal procedure.
12. (350 s) 0.22 ml, i.e. equivalent to Wt A, of a viscoelastic solution with highly viscous properties (Healon5®, Pharmacia, Uppsala, Sweden) was injected into the anterior chamber. The amount injected was equivalent to the initial volume of the anterior chamber.
13. (370 s) Estimation of the capsule volume: The lens capsule was expanded by air injected by a fine graded 0.5 ml syringe and a 27G cannula. Simultaneously the IOP was measured by the pneumatonometer. When an IOP of 20 mmHg was achieved the injection of air was stopped. The sealed capsule guaranteed that no gas leaked out of the capsule at the moment of volume estimation. A volume of 0.26 ml injected air was estimated by the fine graded scaled syringe. The volume of the capsule was approximated to be equivalent to the volume of injected air, i.e 0.26 ml.
14. (410 s) The air introduced into the capsule created an imprint into the viscoelastic solution Additional highly viscous viscoelastic solution (approximately 0.03 ml Healon5) was introduced at a local position into the anterior chamber, positioned 180 degrees to the corneal incision, between the edge of capsulorhexis and the iris, to simulate a desired change of the anterior capsule surface to yield a local refraction change of an intraocular lens implant to be molded in later steps.
15. (530 s) The gas was removed from the capsule gently and simultaneously as 0.26 ml (i.e. the capsule volume estimated earlier) of a lens forming fluid was injected into the capsule, simulated by an injection of 0.26 ml of a fluorescein (5 mg/ml) labeled viscoelastic solution (Healon, Pharmacia, Uppsala, Sweden) using a fine graded scaled syringe.
16. (680 s) The eye was moved from the surgical microscope to the EAS-1000 instrument and a series of slit-lamp photographs was taken in the four different angles (0, 90, 180, 270 degrees in relation to the corneal incision). In the photographs it was revealed that the shape and curvature of the anterior surface of the simulated lens implant (i.e. the fluorescein labeled viscoelastic solution) was very close to a desired design. The locally introduced viscoelastic solution in step 14 had made a local change in the shape of the anterior surface as desired. By the EAS-1000 analysis program the anterior chamber depth was estimated to 2.35 mm, and the anterior curvature of the lens capsule was estimated to 6.54 mm
17. (710 s) 0.05 ml highly viscous viscoelastic solution (Healon5) was injected into the central part of the anterior chamber to flatten the curvature of the anterior surface of the simulated lens implant (i.e. the fluorescein labeled viscoelastic solution), e.g. to compensate for a high refraction rate of the lens material.
18. (840 s) The eye was moved once again from the surgical microscope to the EAS-1000 instrument and a series of slit-lamp photographs was taken in the four different angles (0, 90, 180, 270 degrees in relation to the corneal incision). In the photographs it was revealed that the shape and curvature of the anterior surface of the simulated lens implant (i.e. the fluorescein labeled viscoelastic solution) had received the desired design. By the EAS-1000 analysis program the anterior chamber depth was estimated to 2.60 mm, and the anterior curvature of the lens capsule was estimated to 7.23 mm.

Example 8

Prophylactic Treatment Against PCO, Closing a Capsulotomy, and Molding of an Intraocular Lens Implant A fresh cadaver eye from a newly slaughtered pig (Farmek, Uppsala, Sweden) was used in this experiment to simulate a cataract surgical procedure including prophylactic treatment against PCO, closing a capsulotomy by a patch, and molding of an intraocular lens implant. The eye was maintained in ice-cooled balanced salt solution (BSS®, Alcon Laboratories Inc., Texas, USA) until usage. Hypromellos (Isopto®-Plain, 5 mg/ml, Alcon Laboratories Inc., Puurs, Belgium) was applied topically to rinse the ocular surface and prevent the cornea from drying during the surgery.

The total surgical time is given in brackets after the step number, including the time for the surgical step.

Experimental Surgical Performance

1. A porcine cadaver eye was tempered to body temperature (37° C.) and mounted in a plastic holder by a compress and an o-ring.
2. The IOP (intraocular pressure) was measured by a pneumatonometer (Mentors Model 30 Classic, Mentor O&O, Inc., Norwell, Mass., U.S.A.) and adjusted by stretching-releasing the tightness of the compress and the o-ring until an IOP of 20 mmHg was received.
3. The eye was moved to an EAS-1000 instrument (NIDEK Co Ltd., Japan) and a slit-lamp photograph was taken according to the Scheimpflug principle. The anterior chamber depth was estimated to 2.40 mm (ACD BS) and the anterior lens surface curvature to 6.44 mm by the EAS-1000 analysis program.
4. (0 s) The eye was moved to the surgical microscope (Leica M840, Heerbrugg, Switzerland).
5. (26 s) A clear corneal incision was made close to the edge of limbus with a 3.2 mm angled slit-knife (Sharpoint®, Surgical Specialties Corp, Reading, U.S.A) The tunnel incision was about 2.0 mm in length through the cornea.
6. (45 s) A viscoelastic solution with low viscous properties (Healon®, Pharmacia, Uppsala, Sweden), tempered to room-temperature, was injected into the anterior chamber through the incision, until first signs of anterior chamber overfilling was observed (i.e. leakage from the 3.2 mm incision). The amount of viscoelastic solution introduced into the anterior chamber was estimated by weight to 0.24 g (i.e. the difference in weight of the syringe, estimated before and after the injection; Wt A).
7. (175 s) The eye was moved from the surgical microscope to the EAS-1000 instrument and a slit-lamp photograph was taken. The anterior chamber depth was estimated to 2.52 mm (ACD Healon) and the anterior lens surface curvature to 6.47 mm by the EAS-1000 analysis program. The estimated ACD Healon was close to the previously estimated ACD BS. By this, the amount of injected viscoelastic solution was approximated to be equivalent to the volume of the anterior chamber before surgery, i.e. 0.24 ml.

8. (210 s) A continuous curvilinear capsulorhexis with a diameter of 4 mm was created on the anterior lens capsule by a pair of Corydon forceps (Moria, Paris, France) It was placed close to the iris at the corneal incision, reaching to the central region of the capsule.
9. (250 s) Approximately 0.5 ml balanced salt solution (BSS®) was injected between the lens capsule and the lens, thereby separating the capsule and the lens tissue (i.e. hydro dissection)
10. (390 s) The lens was removed out of the capsule by phacoemulsification (i.e. high frequency ultrasound and continuous flow of irrigation solution (BSS) and continuous aspiration) by an anterior segment operating system equipped with a peristaltic pump system (Oertli Quinto, Oertli Instrumente A G, Berneck, Switzerland; Setting of a vacuum of 150 mmHg, a flow of 25 ml/min, a bottle height of 70 cm, and <70% phaco power at the ultrasound frequency of 28 kHz.)
11. Any remaining viscoelastic solution was removed from the anterior chamber by irrigation and aspiration simultaneously as the lens removal procedure
12. (425 s) 0.24 ml, i.e. equivalent to Wt A, of a viscoelastic solution with highly viscous properties capable to retain gas within the lens capsule (Healon5, Pharmacia, Uppsala, Sweden) was injected into the anterior chamber. The amount injected was equivalent to the initial volume of the anterior chamber.
13. (450 s) The lens capsule was expanded by 0.20 ml air injected by a fine graded 0.5 ml syringe and a 27G cannula.
14. (480 s) The air expanded lens capsule was dried by introducing a device with capillary suction ability to remove any remnants of irrigation solution from the capsule.
15. (600 s) A fiber optic device was introduced into the gas expanded capsule and the surface of the capsule was inspected. No artifacts nor injuries of the capsule was found. However, a local spot of remaining lens fibers and lens epithelial cells of the capsule was identified at a position 90 degrees to the left, using the corneal incision as reference point.
15. (620 s) The gas was removed from the lens capsule by aspiration with a syringe.
16. (640 s) Estimation of the capsule volume: The lens capsule was expanded by air injected by a fine graded 0.5 ml syringe and a 27G cannula. Simultaneously the IOP was measured by the pneumatonometer. When an IOP of 20 mmHg was achieved the injection of air was stopped. The sealed capsule guaranteed that no gas leaked out of the capsule at the moment of volume estimation. A volume of 0.25 ml injected air was estimated by the fine graded scaled syringe The volume of the capsule was approximated to be equivalent to the volume of injected air, i.e. 0.25 ml.
17. (700 s) The local spot of remaining lens tissue was polished/scrubbed with a suitable device.
18. (730 s) Prophylactic treatment against PCO: 0.05 ml of a aqueous solution dyed with phloxine B (10 mg/ml) was applied to the interior surface of the lens capsule by a fine graded 0.5 ml syringe and a 27G cannula with blunted end to simulate application of an active agent solution for treatment of lens epithelial cells. The solution was spread all over the interior surface of the capsule and administered specifically to the lens epithelial cells by assistance of the phenomenon of surface tension, observed in the surgical microscope. A special concern was directed to the spot of remaining lens tissue, to which the tip of the cannula was moved and touched to the surface to improve the administration of the solution. The agent solution was not diluted in the dry environment inside the capsule, i.e. the concentration was remained stable during the treatment.
19. (800 s) After 10 seconds of incubation, the agent solution was washed out of the gas expanded capsule by continuous irrigation of balanced salt solution (BSS) and simultaneous aspiration using the phacoemulsification equipment with an irrigation-aspiration device (Setting of a vacuum of 60 mmHg, a flow of 20 ml/min, a bottle height of 70 cm).
20. (950 s) In order to simulate a removal of an artifact on the posterior lens capsule surface, a 4 mm posterior capsulorhexis was made using a device with a cutting edge.
21. (970 s) The lens capsule was expanded by 0.20 ml of air.
22. (1020 s) The expanded gas filled lens capsule was dried by introducing a device with capillary suction ability to remove any remnants of irrigation solution from the capsule.
23. (1040 s) Additional air (0.05 ml) was injected into the lens capsule.
24. (1130 s) A small portion of glue (Tissucol®) was attached to the surface around the posterior capsulorhexis.
25. (1250 s) A rolled-up plastic membrane (to simulate a transparent membrane suitable for intraocular implantation) was introduced into the gas expanded capsule. The size of the membrane was with a diameter of 6 mm to overlap the edge of the capsulorhexis with about 1 mm.
26. (1370 s) The membrane was unrolled and placed over the posterior capsulorhexis, and securely attached by the glue.
15. (1460 s) The gas was removed from the capsule gently and simultaneously as 0.25 ml (i.e. the capsule volume estimated earlier) of a fluorescein (5 mg/ml) labeled viscoelastic solution (Healon, Pharmacia, Uppsala, Sweden) was injected into the capsule (i.e. simulating an injection of a lens forming fluid) using a fine graded scaled syringe.
16. (1580 s) The eye was moved from the surgical microscope to the EAS-1000 instrument and a series of slit-lamp photographs was taken in the four different angles (0, 90, 180, 270 degrees in relation to the corneal incision). In the photographs it was revealed that the shape and curvature of the anterior surface of the simulated lens implant (i.e. the fluorescein labeled viscoelastic solution) was very close to a desired design. By the EAS-1000 analysis program the anterior chamber depth was estimated to 2.30 mm, and the anterior curvature of the lens capsule was estimated to 6.49 mm.
17. (1640 s) 0.05 ml highly viscous viscoelastic solution (Healon5) was injected into the central part of the anterior chamber to flatten the curvature of the anterior surface of the simulated lens implant (i.e. the fluorescein labeled viscoelastic solution), e g to compensate for a high refraction rate of the lens material.
18. (1800 s) The eye was moved once again from the surgical microscope to the EAS-1000 instrument and a series of slit-lamp photographs was taken in the four different angles (0, 90, 180, 270 degrees in relation to the corneal incision). In the photographs it was revealed that the shape and curvature of the anterior surface of the simulated lens implant (i.e. the fluorescein labeled viscoelastic solution) had received the desired design. By the EAS-1000 analysis program the anterior chamber depth was estimated to 2.52 mm, and the anterior curvature of the lens capsule was estimated to 7.15 mm.

The efficiency of the inventive administration was evaluated visually in the surgical microscope, by slit lamp photography (EAS-1000 instrument) and by dissection. The photographs and the dissected parts were examined visually with respect to distribution and leakage of the test solution.

During the phase of gentle injection of the colored agent solution into the air-filled capsule the solution was distributed all over its inner surface, as being observed in the surgical microscope.

No leakage of the colored substance through the capsulorhexis, i.e. into the anterior chamber, was observed.

EAS-1000 produced slit-lamp photographs made after application also showed that the capsule was colored and that there was no leakage. The same was found when dissecting the lens capsule. Furthermore, the EAS-1000 photographs showed that the molding of a lens forming fluid to an intraocular lens within the capsule is possible to simulate by a fluorescein stained viscoelastic solution (Healon). The fluorescein stained solution in the capsule showed good contrast in the photographs By this, it was possible to simulate that the anterior surface of a lens implant can be formed into a desired shape and curvature by the use of an anterior chamber mold made of a highly viscous viscoelastic solution (Healon5). Desired changes of the curvature of the simulated lens implant was identified in the EAS-1000 produced photographs.

In conclusion, the example indicates that the inventive method administers a small amount of solution efficiently, that is, the treating solution is selectively distributed on the aimed surface. The method also prevents diffusion of the active agent to other not targeted tissues. The example also indicate the benefits of using an intraocular mold within the anterior chamber during the process of forming an intraocular lens molded within the capsule.

Example 9

Example 9 was performed using the method described in Example 8, except for using 1 mg/ml trypan blue (Merck, Germany) instead of Phloxine B in the agent solution. The distribution of the active agent solution was studied by free preparation of the lens capsule.

The results were equal to the ones in Example 8. However, trypan blue was not possible to detect in the EAS-1000 produced slit-lamp photographs, for the reason that trypan blue has no fluoresceive quality as opposed to phloxine B.

Example 10

Example 10 was performed using the method described in Example 9, except for using a rabbit eye in the surgical set up. The surgery was made in the eye of a living rabbit, anaesthetized by 2.0 ml Ketalar® (ketamine 50 mg/ml, Parke-Davis, Barcelona, Spain) and 1.0 ml Rompun® vet (xylazine 20 mg/ml, Bayer A B, Leverkusen, Germany). Tetrakain® (tetrakain 5 mg/ml, Alcon, Puurs, Belgium) was instilled topically for local anesthetics. The pupil was dilated by topical instillation of mydriatics (cyclopentolate 7.5 mg/ml and phenylephrine 2.5 mg/ml, Apoteksbolaget, Umeå, Sweden). After the surgery the rabbit was killed by an intravenous injection of 5 ml of pentobarbital (100 mg/ml, Apoteksbolaget, Malmö, Sweden).

The distribution of the active agent solution was studied by free preparation of the lens capsule.

The results were equal to the ones in Example 9.

Example 11

Implantation of an Intraocular Lens

A fresh cadaver eye from a newly slaughtered pig (Farmek, Uppsala, Sweden) was used in this experiment to simulate a cataract surgical procedure including prophylactic treatment against PCO, closing a capsulotomy by a patch, and molding of an intraocular lens implant. The eye was maintained in ice-cooled balanced salt solution (BSS®, Alcon Laboratories Inc., Texas, USA) until usage. Hypromellos (Isopto®-Plain, 5 mg/ml, Alcon Laboratories Inc., Puurs, Belgium) was applied topically to rinse the ocular surface and prevent the cornea from drying during the surgery.

The total surgical time is given in brackets after the step number, including the time for the surgical step.

Experimental Surgical Performance

1. A porcine cadaver eye was tempered to body temperature (37° C.) and mounted in a plastic holder by a compress and an o-ring.
2. (0 s) The eye was moved to the surgical microscope (Leica M840, Heerbrugg, Switzerland).
3. (25 s) A clear corneal incision was made close to the edge of limbus with a 3.2 mm angled slit-knife (Sharpoint®, Surgical Specialties Corp., Reading, U.S.A). The tunnel incision was about 2.0 mm in length through the cornea.
4. (40 s) A viscoelastic solution with low viscous properties (Healon®, Pharmacia, Uppsala, Sweden), tempered to room-temperature, was injected into the anterior chamber through the incision.
5. (70 s) A continuous curvilinear capsulorhexis with a diameter of 5 mm was created on the anterior lens capsule by a pair of Corydon forceps (Moria, Paris, France). It was placed in the center of the lens capsule.
6. (100 s) Approximately 0.5 ml balanced salt solution (BSS®) was injected between the lens capsule and the lens, thereby separating the capsule and the lens tissue (i.e. hydro dissection).
7. (250 s) The lens was removed out of the capsule by phacoemulsification (i.e. high frequency ultrasound and continuous flow of irrigation solution (BSS®) and continuous aspiration) by an anterior segment operating system equipped with a peristaltic pump system (Oertli Quinto, Oertli Instrumente A G, Berneck, Switzerland; Setting of a vacuum of 150 mmHg, a flow of 25 ml/min, a bottle height of 70 cm, and <70% phaco power at the ultrasound frequency of 28 kHz.)
8. Any remaining viscoelastic solution was removed from the anterior chamber by irrigation and aspiration simultaneously as the lens removal procedure.
9. (310 s) A fluorescein colored viscoelastic solution (approximately 0.2 ml) with highly viscous properties capable to retain gas within the lens capsule (Healon5®, Pharmacia, Uppsala, Sweden) was injected into the anterior chamber.
10. (370 s) The lens capsule was expanded by approximately 0.20 ml air injected by a fine graded 0.5 ml syringe and a 27G cannula.
11. (510 s) An intraocular lens (CeeOn™, model 911, +22.5D, Pharmacia & Upjohn, The Netherlands) was introduced by a pair of forceps through the anterior chamber and into the air-filled capsule.
18. (660 s) The eye was moved from the surgical microscope to the EAS-1000 instrument and a series of slit-lamp photographs was taken in the four different angles (0, 90, 180, 270 degrees in relation to the corneal incision). In the photographs it was shown that the fluorescein labeled viscoelastic solution was present in the anterior chamber, but very little viscoelastic solution was present behind the implanted IOL, which is a fact if the capsule is filled by viscoelastic solution in the standard surgical procedure used today.

The results shown in the photographs indicate the benefit of using a gas expanded capsule during the implantation of an intraocular lens into the capsule, thereby avoiding remnants of viscoelastic solution behind the intraocular lens that otherwise could cause an increase in the post operative intraocular pressure.

It should be understood that the detailed description and specific examples are given by way of example only. Various changes and modifications within the spirit and scope of the invention will become apparent to those skilled in the art from this detailed description.

What is claimed is:

1. A method of performing ocular surgery, after an anterior capsulotomy has been made, by forming a sealed expanded capsular bag including the steps of:

sealing the capsular bag with a viscoelastic material to provide a gas tight seal to prevent leakage into the anterior chamber of the eye during the surgical process;

expanding the capsular bag by introducing a gas capable of exerting a pressure on the inner surface of the capsular bag wall;

inspecting and/or treating the capsular bag with one or several devices and/or agents suitable for performing inspection and/or treatment.

2. The method according to claim 1, wherein the step of inspecting and/or treatment comprises any of:

visual inspection;

estimation of capsular bag volume;

labeling any residual epithelial cells to detect the presence thereof;

removing residual epithelial cells;

implanting one or more intracapsular implants;

injecting a lens forming material for molding a lens in situ;

drying the lens capsule;

alone or in any combination.

3. The method according to claim 2, wherein the implant(s) comprises one or more of capsular rings, intraocular lens, patches, valves, or injectable lens forming fluids.

4. The method according to claim 2, wherein treating the capsular bag according to step c) includes inserting an applicator charged with an agent capable of preventing from PCO.

5. The method according to claim 2, wherein the estimation of the volume of the capsular bag comprises:

measuring the amount of gas injected;

calculating a volume using said measured value.

6. The method according to claim 5, further comprising measuring the intraocular pressure in the capsular bag.

7. The method according to claim 5, further comprising introducing a defined amount of viscoelastic solution into the anterior chamber before injecting the gas into the capsular bag.

8. The method according to 7, wherein the volume of the anterior chamber is measured, and he amount of viscoelastic solution to be introduced into the anterior chamber is taken to be essentially equal to said volume.

9. The method as claimed in claim 5, wherein the amount of gas is estimated by monitoring the flow rate of the gas, and the time of injection.

10. The method according to claim 1, wherein the treatment of step c) includes introduction into the capsular bag of an agent that is capable of preventing PCO from occurring.

11. The method according to claim 10, wherein the active agent is a gas (14).

12. The method according to claim 10, wherein said active agent (15) is injected in form of a solution onto the inner surface of the gas-filled lens capsule (8).

13. The method according to claim 10, wherein the active agent (15) is a colored active agent.

14. The method according to claim 10, wherein the active agent (15) is an active agent to which a dye has been bound.

15. The method according to claim 10, wherein the active agent (15) is in a colored solution.

16. The method according to claim 10, wherein the active agent (15), after having (irreversibly) damaged or killed the lens epithelial cells (9), is inactivated in or removed from the lens capsule (8).

17. The method according to claim 10, further comprising the step of coating the inner surface of the gas-filled lens capsule (11) with a second active agent, capable of preventing cell growth and migration onto the posterior region of the capsule for as long as possible.

18. The method according to claim 17, wherein the addition of the second active agent is subsequent to the addition of the first active agent.

19. The method according to claim 17, wherein both the first and second active agents are administered at the same time.

20. The method according to claim 17, wherein an active agent is administered which has the properties of both the first and the second agent active.

21. The method according to claim 17, wherein the viscoelistic solution (13) has the ability to eliminate the toxicity of the active agents.

22. The method according to claim 10, wherein the agent is selected from doxorubicin, methotrexate, mitomycin, daunomycin/daunorubicin, 5-fluorouracil, colchicines and taxol, and substances usable for performing a photodynamic therapy, e.g. green porphyrin.

23. The method according to claim 1, wherein the expansion of the lens capsule (8) is accomplished with air (14), nitrogen, perfluoropropane, preferably air.

24. The method according to claim 1, wherein the viscoelastic solution (13) has the ability to prevent diffusion of the active agents to adjacent tissues.

25. The method according to claim 1, wherein the medium of step b) is a selected among a gas, an aerosol, or an aqueous fluid.

26. The method according to claim 1, wherein treating the capsular bag involves surgically repairing the bag by attaching a patch of a biocompatible material.

27. The method according to claim 26, wherein the patch of a biocompatible material is made of collagen.

28. The method according to claim 26, wherein the collagen is bovine collagen Type I, III or IV.

29. The method according to claim 26, wherein a fibrin sealant is introduced to secure closure.

30. The method according to claim 26, wherein the patch is located over the anterior capsulotomy with an overlap of at least 1 mm.

31. The method according to claim 26, wherein the patch is located over a posterior capsulotomy with an overlap of at least 1 mm.

32. The method according to claim 1, wherein the natural crystalline lens has been surgically excised including the formation of a capsulorhexis.

33. The method according to claim 32, wherein said capsulorhexis is sealed with a plug that admits entrance into the capsular bag.

34. The method according to claim 32, wherein the method includes insertion of an intraocular lens implant comprising an optical part and haptics capable of securing said implant in the capsular bag.

35. The method according to any of claims 1, 32 or 33 that includes injection of a lens forming fluid into the capsular bag.

* * * * *